United States Patent
Satake et al.

(10) Patent No.: US 7,361,712 B2
(45) Date of Patent: Apr. 22, 2008

(54) WATER ABSORBING AGENT, PROCESS FOR ITS PRODUCTION, AND ABSORBERS AND ABSORBENT ARTICLES MADE BY USING THE AGENT

(75) Inventors: Munekazu Satake, Tokyo (JP); Yoshihisa Ohta, Tokyo (JP)

(73) Assignee: San-Dia Polymers, Ltd., Tokyo (JP)

(*) Notice: Subject to any disclaimer, the term of this patent is extended or adjusted under 35 U.S.C. 154(b) by 335 days.

(21) Appl. No.: 10/495,174

(22) PCT Filed: Nov. 18, 2002

(86) PCT No.: PCT/JP02/12003

§ 371 (c)(1),
(2), (4) Date: Aug. 10, 2004

(87) PCT Pub. No.: WO03/044120

PCT Pub. Date: May 30, 2003

(65) Prior Publication Data

US 2005/0080194 A1   Apr. 14, 2005

(30) Foreign Application Priority Data

Nov. 20, 2001   (JP) .............................. 2001-355395

(51) Int. Cl.
*C08F 20/06* (2006.01)
*C08F 120/02* (2006.01)

(52) U.S. Cl. ................... 525/329.7; 525/383; 525/119; 525/329.9; 525/381

(58) Field of Classification Search ................ 525/383, 525/119, 329.7, 329.9, 381

See application file for complete search history.

(56) References Cited

U.S. PATENT DOCUMENTS 4,666,983 A * 5/1987 Tsubakimoto et al. ...... 525/119
5,883,158 A    3/1999 Nambu et al.

FOREIGN PATENT DOCUMENTS

| EP | 0 618 005 | | 10/1994 |
| EP | 0 618 005 A2 | * | 10/1994 |
| EP | 0 845 272 | | 6/1998 |
| EP | 1 029 886 | | 8/2000 |
| EP | 1 029 886 A2 | * | 8/2000 |
| EP | 1 072 630 | | 1/2001 |
| EP | 1 072 630 A1 | * | 1/2001 |
| EP | 1 325 777 | | 7/2003 |
| JP | 58-180233 | | 10/1983 |
| JP | 59-189103 | | 10/1984 |
| JP | 7-119246 | | 2/1991 |
| JP | 3-179008 | | 8/1991 |
| JP | 10-279693 | | 10/1998 |
| JP | 11-286611 | | 10/1999 |
| JP | 11-349625 | * | 12/1999 |
| JP | 2000-26510 | | 1/2000 |
| JP | 2000-026510 | * | 1/2000 |
| JP | 2000-198853 | | 7/2000 |
| JP | 3118779 | | 10/2000 |
| JP | 2001-079829 | | 3/2001 |
| JP | 2001-089527 | * | 4/2001 |
| JP | 2001-89527 | | 4/2001 |
| JP | 2001-200006 | * | 7/2001 |
| JP | 2001-239159 | * | 9/2001 |

OTHER PUBLICATIONS

Catalogue of Nippon Aerosil Co., LTD., No. 4 (Dec. 1981) and No. 7 (Dec. 1992).
T. Fujimoto, "New Introduction to Surface Active Agents", Sanyo Chemical Industries, Ltd. p. 132, 1985.

* cited by examiner

*Primary Examiner*—Ling-Sui Choi
(74) *Attorney, Agent, or Firm*—Hamre, Schumann, Mueller & Larson, P.C.

(57) ABSTRACT

A water absorbing agent comprising a crosslinked polymer including a water-soluble vinyl monomer (a1) and/or a vinyl monomer (a2) that is formed into the water-soluble vinyl monomer (a1) by hydrolysis, and a crosslinking agent (b) as an essential constituting unit, wherein the following formulae (1) and (2) are satisfied; a process for its production, and absorbers and absorbent articles made by the water absorbing agent.

$$(Y) \geq -1.14(X) + 69.5 \quad (1)$$

$$(X) = ((x1)^2 + 4 \times (x2)^2)^{1/2} \quad (2)$$

wherein (x1) denotes a water-retention amount (g/g) of the water absorbing agent after being soaked in a physiological saline for one hour; (x2) denotes an absorption amount (g/g) of the water absorbing agent after being soaked in a physiological saline under loading of 0.9 psi for one hour; and (Y) denotes a liquid permeation speed (ml/min) of a physiological saline after the water absorbing agent is soaked in a physiological saline under loading of 0.3 psi for one hour. The water-absorbing agent enables easy production of absorbent articles exhibiting high absorption performance in any state, and is suitable for use in disposable diapers, sanitary napkins, and other sanitary goods.

13 Claims, No Drawings

WATER ABSORBING AGENT, PROCESS FOR ITS PRODUCTION, AND ABSORBERS AND ABSORBENT ARTICLES MADE BY USING THE AGENT

TECHNICAL FIELD

The present invention relates to a water absorbing agent, a process for producing the same, and absorbers and absorbent articles made by the water absorbing agent. More particularly, the present invention relates to a water absorbing agent including a crosslinking polymer, which is suitable for absorbent articles, and a method for producing the water absorbing agent.

BACKGROUND ART

Crosslinked polymers in which a water-retention amount is increased by a method of altering and optimizing an amount of polymerization initiators, polymerization temperature and polymerization concentration, and the like, and by a method of using chain transfer agents such as thiol have been proposed (see JP3-179008A). Furthermore, a large number of crosslinking polymers in which absorbing performance or liquid permeability of a swollen gel under loading is enhanced by, for example, a method of treating the vicinity of the surface of polymer particles have been proposed (see Japanese Patent No. 3118779, EP618005A, etc.).

In absorbent articles such as disposable diapers, there is a problem in that when a load is applied, for example, when a user sits down or lies down while wearing such an article, the absorption amount and the absorption speed lower, and as a result, leakage, etc. may occur. Therefore, there have been strong demands for absorbent articles that are free from such a problem and have high absorbing performance regardless of the users' state (even under loading).

That is to say, it is an object of the present invention to provide a water absorbing agent that can be used for absorbent articles that exert high absorbing performance under any conditions (even under loading), a process for its production, and absorbers and absorbent articles made by the water absorbing agent.

The present inventors have investigated in order to achieve the above-mentioned object and have found that the above-mentioned problems can be solved by taking the following points <1> to <3> into consideration:

<1> the water-retention amount after being soaked in a physiological saline for one hour;

<2> the absorption amount of a water absorbing agent after being soaked in a physiological saline under loading of 0.9 psi for one hour; and <3> liquid permeation speed of a water absorbing agent after being soaked in a physiological saline under loading of 0.3 psi (20 g/cm$^2$) for one hour.

SUMMARY OF THE INVENTION

That is to say, the first invention of the present invention relates to a water absorbing agent comprising a crosslinked polymer including a water-soluble vinyl monomer (a1) and/or a vinyl monomer (a2) that is formed into the water-soluble vinyl monomer (a1) by hydrolysis, and a crosslinking agent (b) as an essential constituting unit, wherein the following formulae (1) and (2) are satisfied.

$(Y) \geq -1.14(X) + 69.5$     (1)

$(X) = ((x1)^2 + 4 \times (x2)^2)^{1/2}$     (2)

[In the formulae, (x1) denotes a water-retention amount (g/g) of the water absorbing agent after being soaked in a physiological saline for one hour; (x2) denotes an absorption amount (g/g) of the water absorbing agent after being soaked in a physiological saline under loading of 0.9 psi for one hour; and (Y) denotes a liquid permeation speed (ml/min) of a physiological saline after the water absorbing agent is soaked in a physiological saline under loading of 0.3 psi for one hour.]

The formula (1) expresses the relationship between the water-retention amount and absorption amount under high loading of the water absorbing agent, and the liquid permeability of the swollen gel. Unless the formula (1) is satisfied, absorbent articles having excellent absorbing performance cannot obtained.

The formula (2) is a formula relating to (X) in the formula (1).

Furthermore, the second invention of the present invention relates to a water absorbing agent comprising a crosslinked polymer including a water-soluble vinyl monomer (a1) and/or a vinyl monomer (a2) that is formed into the water-soluble vinyl monomer (a1) by hydrolysis and an internal crosslinking agent (b1) as an essential constituting unit; wherein at least two of the following conditions <1> to <3> are satisfied.

<1> At least one metallic element (c1) selected from the group consisting of Fe, Co, Ni, Cu, Zn, Ru, Rh, Pd, Ag, Cd, Os, Ir, Pt and Au is contained in the amount of $10^{-9}$ to 1 mass % based on the mass of the crosslinked polymer.

<2> Water-insoluble spherical single particles (d) having an average particle size of 1 to 500 nm are contained in the amount of 0.1 to 1 mass % based on the mass of the crosslinked polymer.

<3> Surface crosslinking is carried out with a surface crosslinking agent (b2), and the standard deviation (S) of the absorbance analyzed by infrared absorption spectrophotometry of a carbonyl group or an amino group derived from an ester bond or an amide bond is 15 or less with respect to one particle of the crosslinked polymer.

Furthermore, the third invention of the present invention relates to a method for producing an absorbing agent comprising a crosslinked polymer including a water-soluble vinyl monomer (a1) and/or a vinyl monomer (a2) that is formed into the water-soluble vinyl monomer (a1) by hydrolysis and an internal crosslinking agent (b1) as an essential constituting unit, wherein at least two steps of the following polymerization steps <1> to <3> are included.

<1> A step of polymerization of a crosslinked polymer, including at least one condition selected from the group consisting of (i) to (iii):

(i) the polymerization concentrations of (a1), (a2), other vinyl monomer (a3) capable of co-polymerization and (b1) are $1 \times 10^{-4}$ mass % to 20 mass % based on the total mass of (a1), (a2), (a3), (b1) and a reaction solvent;

(ii) the polymerization temperature is in the range of $(T \pm 5)°$ C. wherein T is 0 to 60; and (iii) the polymerization is carried out in the presence of a complex (c) formed of at least one metal element (c1) selected from the group consisting of Fe, Co, Ni, Cu, Zn, Ru, Rh, Pd, Ag, Cd, Os, Ir, Pt and Au; and a ligand (c2) including an anion and/or a neutral molecule.

<2> A step of mixing water-insoluble spherical single particles (d) having an average particle size of 1 μm to 500 μm with the crosslinked polymer.

<3> A step of surface-crosslinking a crosslinked polymer by a method in which surface crosslinking is carried out with a surface crosslinking agent (b2) to form an ester bond or an amino bond, and the standard deviation (S) of the absorbance analyzed by infrared absorption spectrophotometry of a carbonyl group or an amino group derived from an ester bond or an amide bond is made to be 15 or less with respect to one particle of the crosslinked polymer.

DISCLOSURE OF THE INVENTION

The following is an explanation of the first invention.

The water-retention amount (x1) is a water-retention amount (g/g) of a water-absorbing agent after being soaked in a physiological saline for one hour and is measured by the following method.

Method for Measuring Water-Retention Amount (x1)

1.00 g of samples to be measured are placed in a tea bag (20 cm in length and 10 cm in width) made of a 250-mesh nylon net and soaked in 1000 cc of a physiological saline (concentration: 0.9 mass %) for one hour without stirring. Then, the tea bag was hung for draining saline off for 15 minutes. Then, the tea bag as whole was placed in a centrifugal separator for centrifugal dewatering at 150 G for 90 seconds so as to remove an excess saline, followed by measuring the mass (h1) including the tea bag and calculating the water retention amount (x1) from the following formula. Note here that the temperature of the physiological saline to be used and the measurement atmosphere is 25° C.±2° C.

$$(x1)=\{(h1)-(h2)-1.00\}/1.00$$

wherein (h2) denotes a mass of the tea bag measured by the same operation as mentioned above in the case where no measurement samples are included.

The absorption amount (x2) under loading denotes an absorption amount (g/g) of the absorbing agent after it is soaked in a physiological saline under loading of 0.9 psi for one hour, which is measured by the following method.

Method for Measuring Absorption Amount (x2) Under Loading

In a cylindrical plastic tube (25 mm in inside diameter, and 35 mm in height) with a 250-mesh nylon net affixed on the bottom surface thereof, 0.16 g of samples to be measured is placed and uniformly spread, on which a weight having an outside diameter of 25 mm is placed so that a 0.9 psi load is applied to the samples to be measured. The whole mass (h3) of this cylindrical plastic tube is measured.

The plastic tube containing the samples is soaked in a petri dish (vessel having a diameter of 12 cm) containing 60 ml of a physiological saline with the nylon net side (the side that is soaked in a physiological saline) down for one hour.

Thereafter, the whole mass (h4) of the plastic tube is measured and the absorption amount (x2) under loading is calculated from the following formula. Note here that the temperature of the physiological saline to be used and the measurement atmosphere is 25° C.±2° C.

$$(x2)=\{(h4)-(h3)\}\times 16$$

The permeation speed of the hydrogel denotes a liquid permeation speed (ml/min) of a physiological saline after water absorbing agent is soaked in a physiological saline under loading of 0.3 psi for one hour and is measured by the following method.

Method for Measuring Liquid Permeation speed (Y) of Hydrogel 0.20 g of samples to be measured are soaked in 50 ml of physiological saline for one hour so as to prepare a hydrogel.

On the other hand, a filter-enclosed-type chromatograph tube (diameter: 20 mm, and length: 35 cm) equipped with a cock and a capacity scale is fixed vertically with the cock being dosed and the cock side facing downward.

Then, the above-mentioned hydrogel together with a physiological saline are transferred to the chromatograph tube; a pressure shaft (mass: 15.5 g, and length: 31.5 cm) equipped with a mesh with 149 μm openings is placed in a way in which the mesh side is a hydrogel side; and furthermore a weight (53.0 g) is placed and left to stand for one minute.

The cock at the lower part of the chromatograph tube is opened, the period of time (T1, second) required for a liquid surface inside the tube to be from 40 ml to 20 ml is measured and the liquid permeability speed (Y, ml/min) is calculated from the following formula:

$$(Y)=20(\text{ml})\times 60/(T1-T2)$$

Note here that the temperature of the used physiological saline and the measuring atmosphere is 25° C.±2° C.

(T2) is a value calculated by the same operation as described above in the case where no samples to be measured are included. That is to say, it means the period of time (T2, second) required for a liquid surface inside the tube to be from 40 ml to 20 ml when a physiological saline 50 ml is placed in a filter-enclosed-type chromatograph tube equipped with a cock and a capacity scale.

The formulae (1) and (2) satisfy preferably the formulae (3) and (4); more preferably the formulae (5) and (6); and particularly preferably the formulae (7) and (8). When these formulae are satisfied, it becomes easy to produce absorbent articles exerting high absorbing performance under any conditions.

$$45 \leq (X) \leq 100 \tag{3}$$

$$1 \leq (Y) \leq 75 \tag{4}$$

$$47 \leq (X) < 90 \tag{5}$$

$$1.5 \leq (Y) < 50 \tag{6}$$

$$50 \leq (X) \leq 80 \tag{7}$$

$$2 \leq (Y) \leq 25 \tag{8}$$

The formula (1) preferably is replaced by formula (9), more preferably formula (10), particularly more preferably formula (11), and the most preferably formula (12).

$$(Y) \geq -1.14(X)+71.5 \tag{9}$$

$$(Y) \geq -1.14(X)+73.5 \tag{10}$$

$$(Y) \geq -1.14(X)+75.5 \tag{11}$$

$$(Y) \geq -1.14(X)+77.5 \tag{12}$$

The water-soluble vinyl monomer (a1) is not particularly limited, and vinyl monomer and the like having at least one water-soluble substituent and an ethylenic unsaturated group.

Examples of the water-soluble substituent include a carboxyl (salt) group ($-CO_2M$), a sulfo (salt) group ($-SO_3M$), a group ($-OSO_3M$) for configuring sulfonate (salt), a phosphono (salt) group ($-PO(OM)_2$), a hydroxyl group ($-OH$), an amino group ($-NR_2$), a group ($-CONR_2$) for configuring an amide, an ammonio group ($-NH_3 \cdot Y$) and, mono-, di-, or tri-alkylammonio group ($-NR_3 \cdot Y$), and the like. Herein, "carboxyl (salt) group" is intended to mean a carboxyl group or a carboxylate group (a metal carboxylate group or an ammonium carboxylate group). The same is true for other groups.

Note here that M denotes a hydrogen atom, an alkaline metal (for example, lithium, sodium, potassium, and the like), an alkaline earth metal (for example, magnesium, calcium, and the like), or ammonium ($NH_4$); and R denotes a hydrogen atom or a hydrocarbon group which may include hetero atoms and has a 1 to 4 carbon atoms (for example, methyl, ethyl, propyl, butyl, trifluoromethyl, chloroethyl, and the like); Y denotes a counter anion to an ammonium cation (examples of the counter anion include, for example, chlorine ion, bromine ion, methosulfate ion, sulfate ion, and the like).

An example of the water-soluble vinyl monomer (a1) includes, for example, the following (i) anionic vinyl monomers, (ii) nonionic vinyl monomers, and (iii) cationic vinyl monomers, and the like.

Note here that (i) anionic vinyl monomer may be a salt. An example of anionic vinyl monomer that is salt includes, for example, alkaline metal salt (sodium salt, potassium salt, and the like), alkaline earth metal salt (calcium salt, magnesium salt, and the like), ammonium salt [ammonium salt, tetraalkyl (number of carbon atoms: 1 to 8) ammonium salt (for example, tetraoctyl ammonium and the like) etc.], organic amine salt {alkyl amine having 1 to 8 carbon atoms, alkanolamine having 2 to 8 carbon atoms, polyalkylene (the number of carbon atoms: 1 to 8) polyamine (the number of amino groups: 2 to 10) or derivative of polyalkylamine [a compound that is alkylated with an alkyl group having 1 to 8 carbon atoms, or a compound added by alkylene oxide having 2 to 12 carbon atoms (average number of added moles per one amino group: 1 to 30 moles) etc.]} and the like.

(i) Anionic Vinyl Monomer (i-1) For the vinyl monomer having a carboxyl (salt) group ($-CO_2M$), carboxylic acid (salt) containing a vinyl group having 3 to 30 carbon atoms and the like is used. An example thereof includes unsaturated monocarboxylic acid (e.g., acrylic acid, methacrylic acid, acrylate, methacrylate, crotonic acid, cinnamic acid, and the like); unsaturated dicarboxylic acid (e.g., maleic acid, fumaric acid, citraconic acid, itaconic acid, and the like); and monoalkyl (the number of carbon atoms: 1 to 8) ester of the unsaturated dicarboxylic acid (e.g., monobutyl maleate, monobutyl fumarate, ethylcarbitol monoester of maleic acid, ethylcarbitol monoester of fumaric acid, monobutyl ester of citraconic acid, glycol monoester of itaconic acid, and the like), etc.

(i-2) For vinyl monomer having a sulfo (salt) group ($-SO_3M$), a sulfonic acid (salt) containing a vinyl group having 2 to 30 carbon atoms and the like is used. An example thereof includes aliphatic or aromatic vinyl sulfonic acid (for example, vinyl sulfonic acid, (meth)allyl sulfonic acid, styrene sulfonic acid, α-methyl stylene sulfonic acid, and the like); alkyl sulfonic acid containing (meth)acryloyl ((meth)acryloxy propyl sulfonic acid, 2-hydroxy-3-(meth)acryloxy propyl sulfonic acid, 2-(meth)acryloylamino-2,2-dimethyl ethane sulfonic acid, 3-(meth)acryloxy ethane sulfonic acid, 2-(meth)acrylamide-2-methylpropane sulfonic acid and 3-(meth)acrylamide-2-hydroxypropane sulfonic acid, and the like); and alkyl (the number of carbon atoms: 3 to 18) (meth)allyl sulfosuccinate, and the like.

In the present invention, the terms such as "(meth)acryl . . . " or "(meth)allyl . . . " is intended to mean "acryl . . . " or "methacrylic . . . " for "(meth) acryl," and "allyl . . . " or "methallyl" for "(meth)allyl", respectively.

(i-3) For vinyl monomer having a group including sulfonate (salt) ($-OSO_2M$), sulfuric-acid esterificated hydroxyalkyl (the number of carbon atoms: 2 to 6) (meth)acrylate [for example, sulfuric-acid esterificated hydroxyehyl (meth)acrylate]; sulfuric-acid esterificated poly (polymerization degree: 2 to 30) oxyalkylene (the number of carbon atoms of alkylene group is 2 to 4, and the polymerization form is single or random and/or block) mono (meth)acrylate [for example, sulfuric-acid esterificated poly (polymerization degree: 5 to 15) oxypropylene monomethacrylate]; and compounds expressed by general formulae (13), (14) or (15); and the like is used.

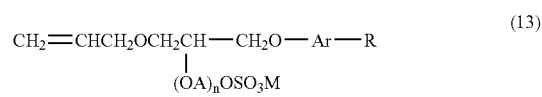

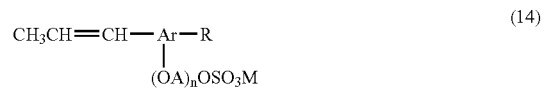

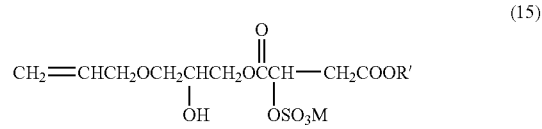

In the above-mentioned general formulae (13) to (15), R denotes a hydrogen atom or an alkyl group having 1 to 15 carbon atoms; and R' denotes a hydrogen atom; an alkyl group having 1 to 15 carbon atoms, which may be substituted by a fluorine atom; an alkaline metal (lithium, sodium, potassium, etc.); an alkaline earth metal (magnesium, calcium, etc.); or ammonium. OA represents oxyalkylene group having 2 to 4 carbon atoms; and when n is 2 or more, two or more OAs may be the same or different; and when the OAs are different, they may be random or block or the mixture thereof; Ar denotes a benzene ring; and M denotes a hydrogen atom, alkaline metal, alkaline earth metal or ammonium; and n denotes an integer from 1 to 50.

An example of an alkyl group includes methyl, ethyl, propyl, t-butyl, 2-ethylhexyl, dodecanyl, and pentadecanyl, etc.

An example of an alkyl group that may be substituted by a fluorine atom includes methyl, ethyl, t-butyl, 2-ethylhexyl, pentadecanyl, trifluoromethyl, and pentafluoroethyl, etc.

An example of an oxyalkylene group includes oxyethylene, oxypropylene, and oxybutylene, etc.

(i-4) An example of a vinyl monomer having a phosphono (salt) group ($-PO(OM)_2$) includes, for example, phosphoric monoester of hydroxyalkyl (the number of carbon atoms: 2 to 6) (meth)acrylate [for example, monophosphate of hydroxyethyl(meth)acrylate, and the like]; phosphoric diester of hydroxyalkyl (the number of carbon atoms: 2 to 6) (meth)acrylate [for example, phenyl-2-acryloyloxyethyl phosphate, and the like]; and (meth)acrylic acid alkyl (the number of carbon atoms: 2 to 6) phosphonic acid [for example, 2-acryloyloxyethyl phosphonic acid, and the like.] etc.

(ii) Nonionic Vinyl Monomer (ii-1) Examples of vinyl monomer having a hydroxyl group (—OH) include, for example, monoethylenic unsaturated alcohol having the 3 to 15 carbon atoms [for example, (meth)allyl alcohol and (meth)propenyl alcohol, and the like]; and monoethylenic unsaturated carboxylic acid ester of polyol having 2 to 6 valences or more (for example, alkylene glycol having 2 to 20 carbon atoms, glycerin, sorbitan, diglycerine, pentaerythritol, polyalkylene number of carbon atoms: 2 to 4) glycol (weight-average molecular weight: 100 to 2000) etc.); monoethylenic unsaturated ether [for example, hydroxyethyl(meth)acrylate, hydroxypropyl (meth)acrylate, triethylene glycol(meth)acrylate, polyoxyethylene-oxypropylene random and/or block, weight-average molecular weight: 100 to 2000) mono (meth)allyl ether (a hydroxyl group at an end may be etherified or esterified by an alkyl (methyl, ethyl and butyl, etc.) group having the number of carbon atoms of 1 to 4) or by a saturated fatty acid (acetic acid and propionic acid, etc.) having the number of carbon atoms of 2 to 3; and the like].

(ii-2) Examples of vinyl monomer having a group ($-CONR_2$) for configuring an amide include, for example, (meth)acrylamide, N-alkyl (the number of carbon atoms: 1 to 8) (meth)acrylamide [for example, N-methyl acrylamide, and the like], N,N-dialkyl (the number of carbon atoms: 1 to 8) acrylamide [for example, N,N-dimethyl acrylamide, N,N-di-n-, or i-propyl acrylamide, and the like], N-hydroxyalkyl (the number of carbon atoms: 1 to 8) (meth)acrylamide [for example, N-methylol(meth)acrylamide, N-hydroxyethyl(meth)acrylamide, etc.]; and N,N-dihydroxyalkyl (the number of carbon atoms: 1 to 8) (meth)acrylamide [for example, N,N-dihydroxyethyl(meth)acrylamide, and the like].

As a vinyl monomer having a group for configuring an amide, other than the above, vinyl lactam having 5 to 10 carbon atoms (for example, N-vinylpyrrolidone, and the like) etc. may be used.

(ii-3) Examples of vinyl monomer having an amino group ($-NR_2$) include an amino group-containing ester of monoethylenic unsaturated mono- or di-carboxylic acid, for example, dialkyl (the number of carbon atoms: 1 to 8) amino alkyl (the number of carbon atoms: 2 to 10) (meth)acrylate, dihydroxyalkyl (the number of carbon atoms: 1 to 8) amino alkyl (the number of carbon atoms: 2 to 10) ester, morpholino alkyl (the number of carbon atoms: 1 to 8) ester, etc. [for example, dimethyl aminoethyl(meth)acrylate, diethyl amino(meth)acrylate, morpholino ethyl(meth)acrylate, dimethyl amino ethyl fumarate, and dimethyl amino ethyl malate, etc.]; amino group-containing amide of monoethylenic unsaturated mono- or di-carboxylic acid, for example, monoalkyl (the number of carbon atoms: 2 to 10) (meth)acrylamide, etc. [dimethyl amino ethyl(meth) acrylamide, diethyl amino ethyl(meth)acrylamide, etc.], and the like.

As a vinyl monomer having an amino group, other than the above, vinylpyridine (for example, 4-vinylpyridine, 2-vinylpyridine, etc.) can be used.

(iii) Cationic Vinyl Monomer (iii-1) Examples of vinyl monomer having an ammonio group ($-NH_3.Y$) include ammonio group-containing ester of monoethylenic unsaturated mono- or di-carboxylic acid [for example, ammonio alkyl (the number of carbon atoms of 2 to 10) (meth)acrylate{ammonio ethyl(meth)acrylate.chloride, etc.} and the like]; ammonio group-containing amide of monoethylenic unsaturated mono- or di-carboxylic acid [for example, ammonio alkyl (the number of carbon atoms of 2 to 10) (meth)acrylamide{ammonio ethyl(meth)acrylamide.methosulfate, etc.} etc.] and the like.

(iii-2) Examples of vinyl monomer having a mono- or di-alkyl ammonio group ($-NRH_2.Y$ or $-NR_2.H.Y$) include alkyl ammonio group-containing ester of monoethylenic unsaturated mono- or di-carboxylic acid [for example, mono alkyl (the number of carbon atoms: 1 to 4) ammonio alkyl (the number of carbon atoms: 2 to 10) (meth)acrylate{methyl ammonio ethyl(meth) acrylate.chloride and t-butyl ammonio ethyl(meth) acrylate.methosulfate, etc.}; dialkyl (the number of carbon atoms: 1 to 4) ammonio alkyl (the number of carbon atoms: 2 to 10) (meth)acrylate{dimethyl ammonio ethyl(meth)acrylate.chloride and methyl t-butyl ammonio ethyl(meth)acrylate.bromide, etc.} etc.]; alkyl ammonio group-containing amide of monoethylenic unsaturated mono- or di-carboxylic acid [for example, monoalkyl ammonio alkyl (the number of carbon atoms of 2 to 10) (meth)acrylamide{methyl ammonio ethyl(meth)acrylamide.chloride and butyl ammonio ethyl(meth)acrylamide.chloride, etc.}; and dialkyl ammonio alkyl (the number of carbon atoms: 2 to 10) (meth)acrylamide{dimethyl ammonio ethyl (meth)acrylamide.chloride and methyl propyl ammonio ethyl(meth)acrylamide.methosulfate, and the like} etc.] etc.

(iii-3) Examples of vinyl monomer having a trialkyl ammonio group ($-NH_3.Y$) include the vinyl monomer having an amino group, which is quaternized by an alkylating agent having 1 to 8 carbon atoms (for example, a quaternization agent such as, for example, methyl chloride, dimethyl sulfuric acid, benzil chloride and dimethyl carbonate, etc.) {for example, trimethyl ammonio ethyl(meth)acrylate.chloride, methyl diethyl ammonio ethyl(meth)acrylate.metho sulfate, trimethyl ammonio ethyl malate-chloride, trimethyl ammonio ethyl(meth)acrylamide.chloride, diethyl benzil ammonio ethyl(meth)acrylamide.chloride} and the like. Other than the above, N-vinylpyridinium salt (for example, N-vinylpyridinium.chloride and N-methyl-2-vinylpyridinium.chloride, etc.) also may be used.

A HLB value of water-soluble vinyl monomer is preferably 10.0 to 20.0, more preferably 11.5 to 20.0, and particularly preferably 13.0 to 20.0.

Note here that the HLB value is a value calculated according to HLB by Davis (Dr. Takehiko Fujimoto, "New Introduction to Surface Active Agents" Copyright 1985, SANYO CHEMICAL INDUSTRIES, LTD, page 132.)

There is no limitation to vinyl monomer (a2) into which the water-soluble vinyl monomer (a1) is formed by hydrolysis. However, vinyl monomer etc. having at least one hydrolysis substituent that becomes a water-soluble substituent by hydrolysis, and the like can be used.

Examples of a hydrolysis group include a group ($-COO-CO-$) for configuring acid anhydride, a group ($-COOR$) for configuring ester, a cyano group, etc.

Note here that R denotes an alkyl (methyl, ethyl and propyl) group having 1 to 3 carbon atoms, a vinyl group, an allyl group and propenyl group.

As the vinyl monomers having a group containing acid anhydride, dicarboxylic acid anhydride etc. having 4 to 20 carbon atoms is used. Examples thereof include maleic anhydride, itaconic acid anhydride, citraconic acid anhydride, and the like.

Examples of vinyl monomer having a group containing ester include, for example, lower alkyl (the number of carbon atoms: 1 to 3) esters of monoethylenic unsaturated carboxylic acid [for example, methyl(meth)acrylate and ethyl(meth)acrylate, etc.], ester of monoethylenic unsaturated alcohol [for example, vinyl acetate, (meth)allyl acetate, etc.] and the like.

Examples of vinyl monomer having a cyano group include a nitrile compound containing a vinyl group having 3 to 6 carbon atoms, etc. [for example, (meth)acrylonitrile, 5-hexene nitrile, and the like], etc.

Hydrolysis may be carried out at any time of during polymerization, after polymerization and both. However, from the viewpoint of the molecular weight of the resultant cross-linked polymer, hydrolysis is preferably carried out after polymerization.

These vinyl monomers (a1) and (a2) may be used singly or in combination of two kinds or more if necessary.

Among them, vinyl monomer is preferably a water-soluble monomer (a1), more preferably anionic vinyl monomer, particularly preferably a vinyl monomer having a carboxyl (salt) group, a sulfo (salt) group, an amino group, a group for configuring amide, an ammonio group or mono; di- or tri-alkyl ammonio group, even more preferably a vinyl monomer having a carboxyl (salt) group or a group for configuring amide, further particularly preferably (meth)acrylic acid (salt) and (meth)acrylamide, and most preferably acrylic acid (salt).

As vinyl monomer used as a constituting unit of a crosslinked polymer that forms a water absorbing agent of the present invention, other vinyl monomer capable of being copolymerized with vinyl monomer (a1) and/or (a2) can be used.

As the other vinyl monomer (a3) capable of being copolymerized hydrophobic vinyl monomer, etc. can be used, but it is not limited thereto.

Examples of the other vinyl monomer (a3) include the following vinyl monomer, etc. (i) to (iii):
(i) aromatic ethylenic monomer having 8 to 30 carbon atoms; a styrene such as styrene; α-methyl styrene, vinyltoluene, and hydroxy styrene, etc.; vinylnaphthalene; a halogen substituted styrene such as dichlorostyrene;
(ii) aliphatic ethylenic monomer having 2 to 20 carbon atoms; alkene [ethylene, propylene, butene, isobutylene, pentene, heptene, diisobutylene, octane, dodecen, octadecene, and the like]; alkadiene [butadiene, isoprene, and the like] etc.
(iii) alicyclic ethylenic monomer having 5 to 10 carbon atoms; monoethylenic unsaturated monomer [pinene, limonene, indene, and the like]; polyethlenic vinyl polymerizable monomer (vinyl polymerizable monomer having two or more ethylenic unsaturated bonds) [cyclopentadiene, bicyclopentadiene, ethylidene norbornane, and the like] etc.

In the case where the other vinyl other monomer (a3) capable of being copolymerized is used, the content of (a3) is preferably 0.01-5 mass %, more preferably 0.05-3 mass %, particularly preferably 0.08-2 mass % and most preferably 0.1-1.5 mass % with respect to the total mass of the vinyl monomer (a1) and (a2). That is to say, in this case, the upper limit of the content of (a3) is preferably 5 mass % more preferably 3 mass %, particularly preferably 2 mass % and most preferably 1.5 mass %. Similarily, the lower limit is preferably 0.01 mass %, more preferably 0.05 mass %, particularly preferably 0.08 mass % and most preferably 0.1 mass %.

The crosslinking agent (b) includes an internal crosslinking agent (b1) used together during polymerization of the vinyl monomer (a1) and/or (a2) and a surface crosslinking agent (b2) for crossliking the surface of the crosslinking particules after polymerization if necessary.

Example of the crosslinking agent (b) include, for example, a crosslinking agent (bb1) having two or more ethylenic unsaturated groups, a crosslinking agent (bb2) having at least one functional group capable of reacting with the water soluble substituent of water-soluble vinyl monomer (a1) and/or the water soluble substituent generated by hydrolysis of vinyl monomer (a2) and having at least one ethylenic unsaturated group, as well as a crosslinking agent (bb3) having at least two functional groups capable of reacting with the water soluble substituent of water-soluble vinyl monomer (a1) and/or the water soluble substituent generated by hydrolysis of vinyl monomer (a2), and the like.

These can be used for any of the internal crosslinking agent (b1) and a surface crosslinking agent (b2).
(i) As the crosslinking agent (bb1) having two or more of ethylenic unsaturated groups, bis(meth)acrylamide having 8 to 12 carbon atoms, poly(meth)acrylate of polyol having 2 to 10 carbon atoms, and poly(meth)allyl ether of polyol having 2 to 10 carbon atoms, and the like are used. Examples thereof include N,N'-methylenebis(meth)acrylamide, ethylene glycol di(meth)acrylate, poly (polymerization degree: 2 to 5) ethylene glycol di-(meth)acrylate, propylene glycol di-(meth)acrylate, glycerin(di- or tri-)acrylate, trimethylolpropane triacrylate, triallyl amine, triallyl cyanurate, triallyl isocyanurate, tetraallyloxy ethane, pentaerythritol triallyl ether and diglycerin di(meth)acrylate and the like
(ii) As the crosslinking agent (bb2) having at least one functional group capable of reacting with the water soluble substituent of water-soluble vinyl monomer (a1) and/or the water soluble substituent generated by hydrolysis of vinyl monomer (a2) and having at least one ethylenic unsaturated group, an ethylenic unsaturated compound having an epoxy group and having 6 to 8 carbon atoms, and an ethylenic unsaturated compound having a hydroxyl group and having 4 to 8 carbon atoms are used. Examples thereof include, for example, glycidyl(meth)acrylate, N-methylol(meth)acrylamide, hydroxyethyl(meth)acrylate, and isocyanate ethyl(meth)acrylate, and the like.
(iii) As the crosslinking agent (bb3) having at least two functional groups capable of reacting with the water soluble substituent of water-soluble vinyl monomer (a1) and/or water soluble substituent of vinyl monomer (a2), polyvalent alcohol, polyglycidyl, polyamine, polyaziridine, polyisocyanate, and the like described in JP 58(1983)-180233A and JP 59-189103A (corresponding U.S. Pat. No. 4,666,983) can be used.

Examples of polyglycidyl compound include ethylene glycol diglycidyl ether, glycerin diglycidyl ether, and the like. Examples of polyamine compound include ethylene diaminie, diethylene triamine, triethylene tetramine, tetraethylene pentamine, pentaethylene hexamine, polyethylene imine and the like. Examples of polyaziridine include "CHEMITITE PZ-33" (trade name) {2,2-bishydroxymethyl butanol-tris(3-(1-azridinyl)propinate)}, "CHEMITITE HZ-22" (trade name) {1,6-hexamethylene diethylene urea}, and "CHEMITITE DZ-22" (trade name) {diphenylmethane-bis-4,4,'-N,N'diethylene urea} (these are trade names of the products of Nippon Shokubai Co., Ltd), etc. Examples of polyisocyanate compound include 2,4-tolylene diisocyanate and hexamethylene diisocyanate, and the like.

These crosslinking agents may be used singly or in combination of two or more kinds of crosslinking agents.

Among the crosslinking agents (b), from the viewpoint of absorption amount of the water absorbing agent, etc. under loading, the internal crosslinking agnet (b1) is preferably a crosslinking agent (bb1) having two or more ethylenic unsaturated groups, more preferably poly(meth)allyl ether of polyol having 2 to 10 carbon atoms, particularly preferably triallyl cyanurate, triallyl isocyanurate, tetraallyloxy ethane, pentaerythritol triallyl ether, and most preferably pentaerythritol triallyl ether.

Among the crosslinking agents (b), as the surface crosslinking agent (b2), from the viewpoint of absorption amount of the water absorbing agent, etc. under loading, the crosslinking agent (bb3) having at least two or more functional groups capable of reacting with the water soluble substituent of water-soluble vinyl monomer (a1) and/or of the water-soluble substituent generated by hydrolysis of vinyl monomer (a2) is preferable, polyglycidyl compound is more preferable, ethylene glycol diglycidyl ether and glycerin diglycidyl ether are particularly preferable, and ethylene glycol diglycidyl ether is most preferable.

The crosslinked polymer that forms the water absorbing agent of the present invention may include both or either of the internal crosslinking agent (b1) and the surface crosslinking agent (b2). Preferably, the crosslinked polymer include both of the internal crosslinking agent (b1) and the surface crosslinking agent (b2).

The amount of the internal crosslinking agent (b1) to be used is preferably 0.001 to 5.0 mass %, more preferably 0.002 to 2 mass %, and particularly preferably 0.003 to 1.6 mass % with respect to the total mass of the vinyl monomer (a1) and/or (a2) as well as the other vinyl monomer (a3) used if necessary. That is to say, the upper limit of the amount of (b1) to be used is preferably 5.0 mass %, more preferably 2 mass %, and particularly preferably 1.6 mass % with respect to the total mass of the vinyl monomer (a1) and/or (a2) as well as (a3) used if necessary. Similarly, the lower limit is preferably 0.001 mass %, more preferably 0.002 mass %, and particularly preferably 0.003 mass %. In this range, water-retention and water absorption capacity is apt to be excellent.

The amount of the surface crosslinking agent (b2) to be used is preferably 0.001 to 7.0 mass %, more preferably 0.002 to 5.0 mass %, and particularly preferably 0.003 to 4.0 mass % with respect to the total mass of the vinyl monomer (a1) and/or (a2) as well as (a3) used if necessary. That is to say, the upper limit of the amount of (b2) to be used is preferably 7.0 mass %, more preferably 5.0 mass %, and particularly preferably 4.0 mass % with respect to the total mass of the vinyl monomer (a1) and/or (a2) as well as (a3) used ifnecessary. Similarly, the lower limit is preferably 0.001 mass %, more preferably 5.0 mass %, and particularly preferably 4.0 mass %.

When the amount of (b2) is not less than the lower limit, the absorption amount under loading tends to be further improved and in the case where the amount of (a2) is less than the upper limit, the crosslinking degree on the surface is not excessive, and the water-retention amount is not likely to be lowered.

A water absorbing agent satisfying the formulae (1) and (2) of the first invention includes a second invention of the present invention.

The following is an explanation of the second invention.

As the water-soluble vinyl monomer (a1), a vinyl monomer (a2) that is formed into the water-soluble vinyl monomer (a1) by hydrolysis and an internal crosslinking agent (b1), those mentioned above can be used and the preferable ranges of them to be used are also the same.

The second invention of the present invention is a water absorbing agent including the above-mentioned crosslinked polymer and satisfying at least two of the above-mentioned requirements <1> to <3>.

The requirements <1> to <3> will be described sequentially. First of all, the requirement <1> will be described.

The metal element (c1) is preferably at least one metal element selected from the group consisting of Fe, Co, Ni, Cu, Zn, Ru, Rh, Pd, Ag, Cd, Os, Ir, Pt and Au; more preferably element: Fe, Co, Ni, Cu, Ru, Rh and Pd; particularly preferably element: Fe, Co, Ni, Ru, Rh and Pd; and most preferably element: Co, Ni, Ru, Ph and Pd.

Preferably, this metal element is present during the production of a crosslinked polymer. More preferably, it is present during the polymerization of the crosslinked polymer. Furthermore, this metal element is preferably derived from the complex (c), which will be described with respect to the third invention mentioned below.

The content of the metal element (c1) is preferably 0.001 ppm to 1 mass % ($10^{-9}$ mass % to 1 mass %); more preferably 0.005 ppm to 0.5 mass % ($5 \times 10^{-9}$ mass % to 0.5 mass %); particularly preferably 0.01 ppm to 0.3 mass % ($10^{-8}$ mass % to 0.3 mass %); further particularly preferably 0.1 ppm to 0.2 mass % ($10^{-7}$ mass % to 0.2 mass %); and most preferably 0.5 ppm to 0.1 mass % ($5 \times 10^{-7}$ mass % to 0.1 mass %) based on the mass of the water absorbing agent of the present invention. That is to say, the upper limit of the content of (c1) is preferably 1 mass %, more preferably 0.5 mass %; and particularly preferably 0.3 mass % based on the mass of the water absorbing agent of the present invention. Similarly, the lower limit is preferably 0.001 ppm, more preferably 0.005 ppm; and particularly preferably 0.01 ppm. When the content is in this range, the water retention amount and the absorption amount under loading is apt to be excellent.

Next, <2> of the second invention will be described.

The average particle size of the water insoluble spherical single particle (d) is preferably 1 to 500 nm; more preferably 3 to 100 nm; particularly preferably 5 to 75 nm; and most preferably 9 to 50 nm. That is to say, the upper limit of the average particle size of (d) is preferably 500 nm; more preferably 100 nm; particularly preferably 75 nm; and most preferably 50 nm. Similarly, the lower limit is preferably 1 nm; more preferably 3 nm; particularly preferably 5 nm; and most preferably 9 nm. The liquid permeability under loading becomes more excellent when (d) is not less than this lower limit. Furthermore, the absorption amount under loading is not likely to be lowered when (d) is less than this upper limit.

It is preferable that the water-insoluble spherical single particle (d) is non-porous. In the case of non-porous water-insoluble spherical single particles, an excellent handling property (particles-fluidity of the resultant water absorbing agent, etc.) is provided.

From the viewpoint of improving the water permeation rate of gel, the specific surface area of the water-insoluble spherical single particle (d) is preferably 20 to 400 $m^2/g$; more preferably 30 to 350 $m^2/g$; and particularly preferably 40 to 300 $m^2/g$. That is to say, the upper limit of the specific surface area of the (d) is preferably 400 $m^2/g$; more preferably 350 $m^2/g$; and particularly preferably 300 $m^2/g$. Similarly, the lower limit of the specific surface area of the (d) is preferably 20 $m^2/g$; more preferably 30 $m^2/g$; and particularly preferably 40 $m^2/g$. When the (d) is in this range, the liquid permeability under loading is likely to become further excellent.

The material of the water-insoluble spherical single particle (d) is not particularly limited as long as it is insoluble in water, is not a metal, and non-reactive with crosslinked polymer. The material may be either an organic substance or inorganic substance. Note here that the metal is not preferable because it may deform the crosslinked polymer through the oxidation-reduction reaction of metal when the crosslinked polymer including the metal is brought into contact with the water.

As the organic substance, (i) organic substance structured by only hydrocarbon; (ii) organic substance structured by carbon, hydrogen and oxygen atoms; (iii) organic substance comprising nitrogen atom; and (iv) other organic substances, and the like can be used.

It is preferable that the melting temperature of a single particle of the organic substance is the drying temperature or higher in order not to allow the single particle of the organic substance to be melted during drying when the crosslinked polymer is dried. As to the balance with respect to the drying temperature, the melting temperature of the organic substance is preferably 130 to 300° C.; and more preferably 150 to 250° C. That is to say, the upper limit of the melting temperature is preferably 300° C. and more preferably 250° C. Similarly, the lower limit is preferably 130° C. and more preferably 150° C.

(i) The organic substance structured by only hydrocarbon includes a substance having the weight-average molecular weight of 10000 to 150000, for example, polyethylene, polypropylene, polystyrene, poly-p-xylylene and polybutadiene, etc.

(ii) The organic substance structured by carbon, hydrogen and oxygen atoms includes a substance having the weight-average molecular weight of 10000 to 150000, for example, polyacrylate, polymethacrylate, polyvinyl acetate, polyvinyl ether, thermoplastic polyester, polycarbonate, polyphenylene oxide, polyepoxy, etc.

(iii) The organic substance comprising nitrogen atom includes a substance having the weight-average molecular weight of 10000 to 150000, for example, polyacrylonitrile, polyamide, thermoplastic polyurethane, etc.

(iv) The other organic substance includes a substance having the weight-average molecular weight of 10000 to 150000, for example, polyvinyl chloride, polyvinylidene chloride, fluororesin, polysulfone, and the like, and substance obtained by copolymerizing two kinds or more of monomer constituting these resins.

Among these substances, the substance (i) is preferable, polystyrene is more preferable, and polystyrene having the weight-average molecular weight of 70000 to 130000 is particularly preferable.

Inorganic substance may be natural inorganic substance and synthetic inorganic substance. Examples of the inorganic substance include oxide such as silicon oxide, aluminum oxide, iron oxide, titanium oxide, magnesium oxide, and zirconium oxide, and the like; carbide such as silicon carbide, aluminum carbide, and the like; and nitride such as titanium nitride, and the like, etc. Furthermore, two or more of these substances may be combined, and a composite of two or more of substances (for example, zeolite and talc, etc.) may be used.

Among these substances, inorganic substance is preferable, oxide is more preferable and silicon oxide is particularly preferably. For the most preferable, silicon oxide is amorphous silicon oxide.

pH of 10 mass % aqueous solution of the water-insoluble spherical single particle (d) is not particularly limited. However, from the viewpoint that primary particles as they are may be present stably and secondary aggregates cannot be formed easily, the pH is preferably 2 to 11, more preferably 2.5 to 10 and particularly preferably 3 to 9. That is to say, the upper limit of the pH of (d) in 10 mass % aqueous solution is preferably 11, more preferably 10 and particularly preferably 9. Similarly, the lower limit is preferably 2, more preferably 2.5 and particularly preferably 3. When the pH is in this range, the stability of (d) is apt to be excellent.

The content of the water-insoluble spherical single particle (d) is preferably 0.1 to 1 mass %: more preferably 0.2 to 0.8 mass %; and particularly preferably 0.4 to 0.6 mass % based on the mass of the crosslinked polymer. That is to say, the upper limit of the content of (d) is preferably 1 mass %; more preferably 0.8 mass %; and particularly preferably 0.6 mass %. Similarly, the lower limit is preferably 0.1 mass %; more preferably 0.2 mass %; and particularly preferably 0.4 mass %. When the content of (d) is not less than this lower limit, the liquid permeability under loading is more preferable. Furthermore, when the content of (d) is less than this upper limit, the liquid permeability under loading is more preferable and at the same time mechanical strength of the water absorbing agent tends to be increased.

Next, <S> of the second invention will be described.

The standard deviation (S) of absorbance with respect to one crosslinked polymer analyzed by infrared absorption spectrophotometry for a carboxyl group and/or an amino group derived from an ester bond or an amide bond generated by reacting the surface crosslinking agent (b2) with a crosslinked polymer is preferably 15 or less, more preferably 10 or less, further preferably 5 or less, further particularly preferably 3 or less, and most preferably 2 or less.

When the standard deviation is in this range, in surface-crosslinking of the crosslinked polymer with the surface crosslinking agent (b2), the vicinity of the surface of the crosslinked polymer particles is uniformly crosslinked on the surface. Thus, it is possible to improve the absorption amount under loading significantly without lowering the water-retention amount of the water absorbing agent.

The method for measuring the standard deviation of the absorbance analyzed by infrared absorption spectrophotometry is carried out as follows.

<Method for Measuring Standard Deviation of Absorbance>

The particle size of the crosslinked polymer particles is adjusted by using sieves with 105 μm to 710 μm mesh openings, and the crosslinked polymer particles that do not pass through the sieve with 105 μm but pass through the sieve with 710 μm are collected. Then, the absorbance of carbonyl groups and/or amino groups in a 10×10×10 μm-region on the crosslinked polymer surface was measured by using Fourier transform infrared spectrophotometer (for example, "FTIR-8200PC," product of Shimadzu Corporation). Similarly, 100 different points in a region of the same particles are measured and the standard deviation (S) of the measurement value was calculated. Note here that the standard deviation (S) can be calculated by the following formula (16).

$$(S) = ((100\Sigma p^2 - (\Sigma p)^2)/100(100-1))^{1/2} \quad (16)$$

In the above-mentioned formula, p denotes a absorbance measured by an infrared spectrophotometer.

When at least two of the above-mentioned <1> to <3> are satisfied, the water-retention amount (x1) and the absorption amount under loading (x2) and the liquid permeability under loading (Y) of the water absorbing agent tend to increase, and thus the absorbing performance of the water absorbing agent becomes excellent.

On the other hand, among <1> to <3> mentioned above, when only one is satisfied, any of the water-retention amount (x1), the absorption amount under loading (x2) and the liquid permeability under loading (Y) of the water absorbing agent tend to be lowered, and thus it is not preferable.

More specifically, when <1> is not satisfied, the water-retention amount (x1) and the absorption amount under loading (x2) tend to be lowered; when <2> is not satisfied, the absorption amount under loading (x2) or the liquid permeability under loading (Y) tends to be lowered; and when <3> is not satisfied, any of the water-retention amount (x1), the absorption amount under loading (x2) and the liquid permeability under loading (Y) tends to be lowered.

The water absorbing agent of the first invention or the second invention of the present invention can be produced by applying the conventionally known methods. However, preferably they are produced by the following production method that is the third invention of the present invention.

Next, the third invention will be described.

For the water-soluble vinyl monomer (a1) and vinyl monomer (a2) that is formed into the water-soluble vinyl monomer (a1) by hydrolysis and internal crosslinking agent (b1), the above-mentioned materials can be used and the preferable ranges thereof are the same.

The third invention of the present invention is a method for producing a water absorbing agent (including the above-mentioned crosslinked agent), wherein at least two steps of the above-mentioned steps of the following polymerization steps <1> to <3> are included.

The steps <1> to <3> will be described sequentially.

The step <1> related to a polymerization step by the method including at least one condition selected from the group consisting of the following (i) to (iii).

(i) the polymerization concentration of vinyl monomers (a1), (a2), (a3) and crosslinking agent (b1) is preferably $1 \times 10^{-4}$ to 20 mass % based on the total mass of (a1), (a2), (a3), (b1) and a reaction solvent, more preferably 1 to 18 mass %, and particularly preferably 5 to 15 mass %. That is to say, the upper limit of the polymerization concentration is preferably 20 mass %, more preferably 18 mass % and particularly preferably 15 mass % based on the total mass of (a1), (a2), (a3), (b1) and a reaction solvent. Similarly, the lower limit is preferably $1 \times 10^{-4}$ mass %, more preferably 1 mass % and particularly preferably 5 mass %. When the concentration is in this range, the absorption amount (x2) and the water-retention amount (x1) tends to become excellent.

(ii) the polymerization temperature is preferably in the range of $(T \pm 5)°$ C. (T is 0 to 60); more preferably in the range of $(T \pm 4)°$ C. (T is 0 to 60); particularly preferably in the range of $(T \pm 3)°$ C. (T is 0 to 60), and most preferably in the range of $(T \pm 2)°$ C. (T is 0 to 60). When the polymerization temperature is in this range, the absorption amount under loading (x2), water-retention amount (x1), and liquid permeability under loading (Y) are improved.

Herein, the phrase "the polymerization temperature is in the range of $(T \pm 5)°$ C. (T is 0 to 60)" means that firstly the target polymerization temperature T is determined to be any temperature from 0 to 60° C. and then when T is determined to be a specific temperature, the polymerization is preferably carried out in the range at the specific temperature $\pm 5°$ C. That is to say, it means that it is preferable that the polymerization is carried out while controlling the temperature without largely changing from the specific temperature T.

(iii) It is preferable that at least one metallic element (c1) selected from the group consisting of Fe, Co, Ni, Cu, Zn, Ru, Rh, Pd, Ag, Cd, Os, Ir, Pt and Au is the same as that mentioned above.

The ligand (c2) for the complex (c) is not particularly limited as long as it is a ligand that comprises an anion or a neutral molecule. Examples of the ligand (c2) include [1] hydrido hydrogen anion) and halogen anion (fluorine anion, chlorine anion, and bromine anion, etc.), [2] a compound containing at least one element selected from the group consisting of nitrogen, oxygen, phosphorus, and sulfur, and [3] a conjugated compound, and the like.

As [2] the compound containing at least one element selected from the group consisting of nitrogen, oxygen, phosphorus and sulfur, the following (1) to (11) are used. (1) a tertiary phosphine compound having 1 to 4 or more phosphorus atoms and 3 to 42 or more carbon atoms; (2) an ammonia or amine having 1 to 4 or more of nitrogen atoms and 1 to 44 or more carbon atoms; (3) a compound containing a carbonyl group (excluding carboxylic acid) having 1 to 3 or more carbonyl groups and 3 to 40 or more carbon atoms; (4) a carboxylic acid having 1 to 4 or more carboxyl groups and 2 to 20 or more carbon atoms; (5) an oxime having 1 to 4 or more groups (>C=N—OH) for configuring the oxime and 2 to 20 or more carbon atoms; (6) a phenol having 1 to 4 or more hydroxyl groups and 6 to 30 or more carbon atoms; (7) an ether having 1 to 8 or more ether bonds (—O—) and 4 to 30 or more carbon atoms; (8) a sulfur compound having 1 to 4 or more sulfur atoms and 2 to 40 or more carbon atoms; (9) an amide having 1 to 3 or more groups for configuring the amide and 3 to 54 or more carbon atoms; (10) an N-oxide having 1 to 3 or more groups (—N—O) for configuring N-oxide and 6 to 20 or more carbon atoms; and (11) others.

Examples of (1) the tertiary phosphine compound having 1 to 4 or more phosphorus atoms and 3 to 43 or more carbon atoms include: trimethylphosphine, triethylphosphine, diethylphenylphosphine, triphenylphosphine (hereinafter abbreviated as "PPh3"), ortho-phenylene bis(diphenylphosphine), ortho-phenylene bis(dimethylphosphine), ortho-phenylene bis(diethylphosphine), ortho-phenylene bis(ethylphenylphosphine), 1,2-bis(diphenylphosphino)ethane, 1,2-bis(dimethylphosphino)ethane (hereinafter abbreviated as "dppe"), 1,2-bis(diethylphosphino)ethane, 1,2-bis(ethylphenylphosphino)ethane, 1,2-bis(diphenylphosphino)methane (hereinafter, will be referred to as "dppm"). 1,2-bis(dimethylphosphino)methane, 1,2-bis(diethylphosphino)methane, 1,2-bis(ethylphenylphosphino)methane, tris(diphenylphosphino ethyl)phosphine, tris(diethylphosphino ethyl)phosphine, tris(dimethylphosphino ethyl)phosphine, tris(ethylphenylphosphino ethyl)phosphine, and the like.

Examples of (2)ammonia or amine having 1 to 4 or more nitrogen atoms and 1 to 44 or more carbon atoms include: (2-1)amine having one nitrogen atom, (2-2)amine having two nitrogen atoms, (2-3)amine having three or more nitrogen atoms, and the like.

Examples of (2-1)amine having one nitrogen atom include pyridine (hereinafter abbreviated as "py"), diethylamine, salicylamine, aminoethaneselenol, 2-hydroxy-6-methylpyridine, 2-diethylamino ethanol, bis(2-aminoethyl) amide, ethanolamine, 2-aminoethanol, β-alanine, 2-hydroxy-6-methylpyridine, 3-salicylideneamino-1-propanol, 2-pyrrolidone, 8-quinolinol, salicylaldimine, α-picoline, and the like.

Examples of (2-2)amine having two nitrogen atoms include ethylene diamine (hereinafter abbreviated as "en"). propylene diamine, trimethylenediamine, 1,2-cyclohexane diamine, N,N-diethyl ethylene diamine, N,N-dimethyl ethylene diamine, salicylidene ethylene diamine, N-ethylsalicylal diamine, bis(benzoylacetone)ethylene diamine, 1,2-diamino-1,1'-dimethylethane, 2,2'-bipyridine (hereinafter abbreviated as "bpy"), 2,2'-bipyridine-3-yne, 2, 2'-bipyridine-N,N'-dioxide, dicyandiamidine, (aminoimino methyl) urea, [(2-aminoethyl)amino]-1-propanol, 2-[(3-aminopropyl)amino]ethanol, N-2[2-(diethylamino)ethyl]-3amino-1-propanol, tris[2-(methylamino)ethyl]amine, imidazole, N,N'-disalicylidene trimethylene diamine, 4,6,6-trimethyl-3, 7-diazanona-3-en-1,9diol, N,N,N',N'-tetramethyl ethylene diamine, 1, 8-naphthyridine, and the like.

Examples of (2-3)amine having three or more nitrogen atoms include diethylene triamine, triethylene tetramine, tetraethylpentamine, N, N'-bis(2-aminobenzylidene)ethylene diamine, tris[2-(methylamino)ethyl]amine, diaminopyridine, 1,2-bis[bis(2-pyridyl ethyl)aminomethyl]benzene, 4-dimethylamino-2,3-dimethyl-1-phenyl-5-pyrazolane, biguanide, imide dicarboneimde diamide, biuret, carbamoyl guanidine, phthalocyanine, N,N,N', N'-tetrakis(2-aminoethyl)ethylene diamine, 1,2,3-triaminopropane, tris(2-benzimidazolylmethyl)amine, tetrakis(2-pyridyl methyl) ethylene diamine, 2,2',2'-terpyridine, 1,4,7,10-tetraazadecane, 1,4,8, 11-tetraazaundecane, 1,5,8,12-tetraazadodecane, 1,4, 8, 11-tetraazacyclotetradecane, ethylene bis(biguanide), tetraphenylporphyrin, tris (2-pyridyl methyl)amine, histidine, and the like.

Examples of (3) the compound containing a carbonyl group (excluding carboxylic acid) having 1 to 3 or more carbonyl groups and 3 to 40 or more carbon atoms include ethyl acetate, acetylacetone (hereinafter abbreviated as "acac"), 2, 4-pentanedione, bis(acetylacetone), 3-methylpentane-2,4-dione, 1-phenyl-1, 3-butanedione, 3-phenylpentane-2,4-dione, 1,3-diphenyl-1,3-propanedione, 1-phenyl-1,3,5-hexanetrione, 5,5'-(1,2-ethane diyldinitrilo)bis(1-phenyl-1, 3-hexanedione), trifluoro acetylacetone, hexafluoroacetylacetone, benzyl, dibenzoyl methane, asparaginebenzoyl acetone, thenoyl trifluoro acetone, 4,4-(1,2-ethane diyldinitrilo)bis(2-pentanone), dipivaloylmethane, and the like.

Examples of (4) the carboxylic acid having 1 to 4 or more carboxyl groups and 2 to 20 or more carbon atoms include oxalic acid, malonic acid, salicylic acid, phthalic acid, nicotinic acid, picolinic acid, aspartic acid, benzoyl pyruvic acid, ethylenediamine diacetic acid, nitrilotriacetic acid, N'-(2-hydroxyethyl) ethylenediamine triacetic acid, propylene diamine tetraacetic acid, ethylenediamine tetraacetic acid, trans-1,2-cyclohexane diamine tetraacetic acid, trans-1,2-(cyclohexane dinitrilo)tetraacetic acid, (1,2-ethane diyldinitrilo)tetraacetic acid, ethylenediamine tetraproprionic acid, glycine, N-methyl glycine, glycylglycine, glycyl glycyl glycyl glycine, salicylidene glycine, imino diacid, methyl iminodiacetic acid, N,N-diethyl diseleno carbamic acid, methionine, proline, sarcosine, xanthogenic acid and the like.

Examples of (5) the oxime having 1 to 4 or more groups (>C=N—OH) for configuring the oxime and 2 to 20 or more carbon atoms include: dimethyl glyoxime, 3-(2-amino ethyl imino)-2-butanone oxime, benzilmethyl glyoxime, 2, 6-diacetylpyridine dioxime, 2-pyridyl aldoxime,3-phenyl imino-2-butanone oxime, salicyl aldehyde oxime, and the like.

Examples of (6) the phenol having 1 to 4 or more hydroxyl groups and 6 to 30 or more carbon atoms include: catechol, 1,2-benzenediol, 1,3-bis[bis(2-pyridyl ethyl)aminomethyl]phenol, 2,6-bis[bis(2-pyridyl ethyl)aminomethyl]-4-phenol, 1-nitroso-2-naphthol, and the like.

Examples of (7) the ether having 1 to 8 or more ether bonds (—O—) and 4 to 30 or more carbon atoms include: tetrahydrofuran, 1,4-dioxane, tetrahydrofuran, 1,4,7,10-tetraoxacyclotetradecane, 1,4,7,10,13-pentaoxacyclopentadecane, 1,4, 7,10,13,16-hexaoxycyclooctadecane, 4,7,13,16-tetraoxa-1, 10-diazacyclooctadecane, 4,7,13,18-tetraoxa-1, 10-diazabicyclo[8,5,5]icosane, 2, 3-benzo-1,4,7,10,13-pentaoxacyclopentade-2-cene, 4,7,13,16,21-pentaoxa-1, 10-diazabicyclo[8,5,5]trichosan, monensin, nigericin, and the like.

Examples of (8) the sulfur compound having 1 to 4 or more sulfur atoms and 2 to 40 or more carbon atoms include: diethyl dithiocarbamic acid, ethylthio glycol acid, ethylene bisthio glycol acid, ethylene thiourea, phenyldithio acetoc acid, dithio benzoic acid, 1,2-aminoethnethiol, diphenylthiocarbazone, dimethylsulfoxide, 2,4-pentanedithion, 2,2,7, 7-tetramethyl-3,6-dithiaoctane, 2-imidazolidinethione, dimethyl dithiocarbamic acid, thiourea, cysteine, maleonitrile dithiol, and 1,4,8,11-tetrathiaundecane, and the like.

Examples of (9) the amide having 1 to 3 or more groups for configuring the amide and 3 to 54 or more carbon atoms include: diazo amide, N,N-dimethyl acetamide, N,N-dimethyl formamide, hexamethyl triamide phosphate, diphenyl phosphinic acid amide, amionethylamide, oxamide, valinomycin, phthalimide, succinimide, valinomycin, and the like.

Examples of (10) the N-oxide having 1 to 3 or more groups of N-oxide (—N—O) and 6 to 20 or more carbon atoms include: α-picoline-N-oxide, γ-picoline-N -oxide, pyridine-N-oxide, and the like.

Examples of (11) the others include: nitrogen molecule, water, carbon monoxide, urea, salicyl aldehyde, N-nitrosophenyl hedroxyl amino acid hydrogen, and the like.

[3] As a conjugated compound, a conjugated compound having 2 to 10 or more unsaturated groups and 4 to 14 or more carbon atoms is used. Examples of the conjugated compound include 1,5-cyclooctadiene (hereinafter, abbreviated as "cod"), 1,3,5,7-cyclooctatetraene, cyclopentadienyl, pentamethyl cyclopentadienyl, tropolone, 1,10-phenanthroline, and the like.

Among these ligands, from the viewpoint of polymerization, halogen (fluorine, chlorine, bromine, iodine) anion and a compound containing a phosphorus element are preferable. Chlorine anion, bromine anion, iodine anion, and tertiary phosphine compound are more preferable. Chlorine anion, bromine anion, and tertiary phosphine compound are particularly preferable. Chlorine anion and a tertiary phosphine compound are most preferable.

The form of coordination of the ligand (c2) is not particularly limited and may include unidentate ligand (examples of such ligand include triphenylphosphine), bidentate ligand (examples of such ligand include ethylene diamine), multidentate (3-6 dentate) ligand (examples of such ligand include terpyridine), and combination thereof.

Furthermore, (c) may be any of a non-electrolyte complex having no electric charges, cationic complex having positive electric charge and anionic complex having a negative electric charge.

Preferable specific examples of complex (c) include the following complexes.

(1) When the metallic element (c1) is a metallic element in Group 11 of the periodic table, the preferable examples include: $[Cu(CH_3)(PPh_3)]$, $[Cu_2Cl(cod)_2]$, $[Ag(py)_2]Cl$, $[Ag(py)_4]Cl$, $[Ag(py)_4]Cl_2$, $[AuCl(PPh_3)]$, $[AuCl_3(PPh_3)]$, $[Au(dppe)]Cl$, and the like.

(2) When the metallic element (c1) is a metallic element in the fourth period Group 8 to 10 of the periodic table, the preferable examples include: $[FeCl_2(bpy)_2]$, $[FeCl_2$ $(bpy)_2]Cl$, $[FeCl(H)(CO)(PPh_3)_3]$, $[FeCl(H)(dppe)_2]$, $[FeCl_3(NO)(PPh_3)_2]$, $[FeCl_2(PPh_3)_3]$, $[FeCl_2(PPh_3)_3]$, $[Fe(CN)_2(bpy)_2]$, $[Fe(CO)_2(PPh_3)_3]$, $[Fe(H)_2(N_2)(PPh_3)_3]$, $[Co_2Cl_2(cod)_2]$, $[CoCl(CO)(PPh_3)_2]$, $[CoCl(PPh_3)_3]$, $[CoCl(O_2)(PPh_3)_3]$, $[CoCl_3(py)_3]$, $[Co(cod)_2]Cl$, $[Co(H)(CO)(PPh_3)_3]$, $[Ni(acac)Cl(PPh_3)]$, $[NiBr(CH_3)[P(C_2H_5)_3]_2]$, $[NiBr(NH_3)_3]$, $[Ni(CH_3)Cl(cod)]$, $[Ni(C_2H_5)(cod)]Cl$, $[Ni(CH_3)(PPh_3)]$, $[Ni_2Cl_2(acac)_2]$, $[NiCl_2(bpy)]$, $[NiCl_2(cod)]$, $[Ni_2Cl_2(dppm)]$, $[NiCl_2(en)]$, $[NiCl_2(NH_3)(PPh_3)]$, $[NiCl_2(PPh_3)]$, $[Ni_2Cl_4(PPh_3)_2]$, $[Ni(PPh_3)_4]$, $[Ni(py)_4]Cl_2$, $[Ni(SO_3)(H_2O)_3]$, $[Ni(SO_3)(NH_3)_3]$, and the like.

(3) When the metallic element (c1) is a metallic element in the fifth period Group 8 to 10 of the periodic table, the preferable examples include: $[Rh_2Cl_2(cod)_2]$, $[RhCl(CO)(PPh_3)_2]$, $[RhCl(PPh_3)_3]$, $[RhCl(O_2)(PPh_3)_3]$, $[RhCl_3(py)_3]$, $[Rh(cod)_2Cl]$, $[Rh(H)(CO)(PPh_3)_3]$, $[RuCl_2(bpy)_2]$, $[RuCl_2(bpy)_2]Cl$, $[RuCl(H)(CO)(PPh_3)_3]$, $[RuCl(H)(dppe)_2]$, $[RuCl_3(NO)(PPh_3)_2]$, $[RuCl_2(PPh_3)_3]$, $[RuCl_2(PPh_3)_4]$, $[Ru(CN)_2(bpy)_2]$, $[Ru(CO)_2(PPh_3)_3]$, $[Ru(H)_2(N_2)(PPh_3)_3]$, $[Pd(acac)Cl(PPh_3)]$, $[PdBr(CH_3)[P(C_2H_5)_3]_2]$, $[PdBr(NH_3)_3]$, $[Pd(CH_3)Cl(cod)]$, $[Pd(C_2H_5)(cod)]Cl$, $[Pd(CH_3)(PPh_3)]$, $[Pd_2Cl_2(acac)_2]$, $[PdCl_2(bpy)]$, $[PdCl_2(cod)]$, $[Pd_2Cl_2(dppm)]$, $[PdCl_2(en)]$, $[PdCl_2(NH_3)(PPh_3)]$, $[PdCl_2(PPh_3)]$, $[Pd_2Cl_4(PPh_3)_2]$, $[Pd(PPh_3)_4]$, $[Pd(py)_4]Cl_2$, $[Pd(SO_3)(H_2O)_3]$, $[Pd(SO_3)(NH_3)_3]$, and the like.

(4) When the metallic element (c1) is a metallic element in the sixth period Group 8 to 10 of the periodic table, the preferable examples include: $[OsCl_2(bpy)_2]$, $[OsCl_2(bpy)_2]Cl$, $[OsCl(H)(CO)(PPh_3)_3]$, $[OsCl(H)(dppe)_2]$, $[OsCl_3(NO)(PPh_3)_2]$, $[OsCl_2(PPh_3)_3]$, $[OsCl_2(PPh_3)_4]$, $[Os(CN)_2(bpy)_2]$, $[Os(CO)_2(PPh_3)_3]$, $[Os(H)_2(N_2)(PPh_3)_3]$, $[Ir_2Cl_2(cod)_2]$, $[IrCl(CO)(PPh_3)_2]$, $[IrCl(PPh_3)_3]$, $[IrCl(O_2)(PPh_3)_3]$, $[IrCl_3(py)_3]$, $[Ir(cod)_2Cl]$, $[Ir(H)(CO)(PPh_3)_3]$, $[Pt(acac)Cl(PPh_3)]$, $[PtBr(CH_3)[P(C_2H_5)_3]_2]$, $[PtBr(NH_3)_3]$, $[Pt(CH_3)Cl(cod)]$, $[Pt(C_2H_5)(cod)]Cl$, $[Pt(CH_3)(PPh_3)]$, $[Pt_2Cl_2(acac)_2]$, $[PtCl_2(bpy)]$, $[PtCl_2(cod)]$, $[Pt_2Cl_2(dppm)]$, $[PtCl_2(en)]$, $[PtCl_2(NH_3)(PPh_3)]$, $[PtCl_2(PPh_3)]$, $[Pt_2Cl_4(PPh_3)_2]$, $[Pt(PPh_3)_4]$, $[Pt(py)_4]Cl_2$, $[Pt(SO_3)(H_2O)_3]$, $[Pt(SO_3)(NH_3)_3]$, and the like.

Among the above, the case where (3) the metallic element (c1) is a metallic element in the fifth period Group 8 to 10 of the periodic table, the preferable examples is preferable.

From the viewpoint of the polymerization property and operationability, the preferable example of the complex (c) is a complex compound capable of being dissolved in water or water-soluble organic solvent ($[RhCl(PPh_3)_3]$, $[RuCl_2(PPh_3)_3]$, $[RuCl_2(PPh_3)_4]$, $[Pd(acac)Cl(PPh_3)]$, $[Pd_2Cl_2(acac)_2]$, $[PdCl_2(PPh_3)]$, and $[Pd_2Cl_4(PPh_3)_2]$, etc.).

As the water soluble organic solvent, the same organic solvent that is used for synthesizing (c) mentioned below can be used.

These complexes (c) can be produced by the known methods, for example, the method described in Angew. Chem. Int. Ed. Engl.,12,57 (1973); J.Chem. Educ., 50,343 (1973); Accts. Chem. Research, 3, 105 (1970); Chm. Rev., 73, 487 (1973); Interscience-Wilry (1968); Chem. Soc. Rev., 4,27 (1975); "Basic Inorganic Chemistry" (F. A. Cotton and G. Willkinson, BAIFUKAN CO., LTD); and "Dictionary for Inorganic Compounds/Complex" (Katsuyoshi NAKAHARA, Kodansha Ltd.) etc.

As a simpler method, for example, the complex can be produced by mixing a salt of a metallic element (c1) (for example, metal halide, etc.) and ligand (c2) at room temperature. Furthermore, there is a method including producing another intermediate complex compound and then producing the targeted complex compound. A salt of a metallic element (c1) and a ligand (c2) may be mixed as it is or mixed after dissolving (c1) and (c2) into an aqueous solution/solvent solution, or mixed in an aqueous solution/solvent solution. If necessary, they may be heated to 30 to 200° C. If materials to be removed are generated, they may be removed under reduced pressure. The generated complex (c) may be taken out as it is or as a crystal and may be purified. Examples of solvent to be used herein include, alcohol (methanol, ethanol, etc.), ketone (acetone, methylethylketone, etc.), amide (N,N'-dimethyl formamide, N-methyl pyrrolidone, etc.), sulfoxide (dimethylsulfoxide, etc.), and mixture of two or more of these materials.

When the complex (c) is used, the amount to be used is preferably 0.005 ppm to 2 mass % ($5 \times 10^{-9}$ mass % to 2 mass %), more preferably 0.01 ppm to 1 mass % ($10^{-8}$ mass % to 1 mass %), particularly preferably 0.02 ppm to 0.6 mass % ($2 \times 10^{-8}$ to 0.6 mass %), further particularly preferably 0.03 ppm to 0.2 mass % ($3 \times 10^{-8}$ mass % to 0.2 mass %), and most preferably 0.05 ppm to 0.1 mass % ($5 \times 10^{-8}$ to 0.1 mass %) based on the total mass of vinyl monomer (a1), (a2), (a3) and internal crosslinking agent (b1). That is to say, the upper limit of the amount to be used is preferably 2 mass %, more preferably 1 mass %, particularly preferably 0.6 mass %, further particularly preferably 0.2 mass %, and most preferably 0.1 mass %. Similarly, the lower limit is preferably 0.005 ppm, more preferably 0.01 ppm, particularly preferably 0.02 ppm, further particularly preferably 0.03 ppm, and most preferably 0.05 ppm. When the amount to be used is in this range, the performance as absorbent articles is furter improved and polymerization speed and polymerization rate can be firther improved, and the productivity can become more excellent.

In the step <2> of the third invention, the average particle size, the specific surface area, material and pH in 10 mass % aqueous solution of the water-insoluble spherical single particles (d) are the same as those in <2> of the second invention. And the preferable ranges are also the same. The amount of the water-insoluble spherical single particles (d) to be used is preferably 0.1 to 1 mass %, more preferably 0.2 to 0.8 mass %, and particularly preferably 0.4 to 0.6 mass % based on the mass of the crosslinked polymer. That is to say, the upper limit of the amount of (d) to be used is preferably 1 mass %, more preferably 0.8 mass %, and particularly preferably 0.6 mass %. Similarly, the lower limit is preferably 0.1 mass %, more preferably 0.2 mass %, and particularly preferably 0.4 mass %. When the amount is this lower limit or more, the liquid permeability under loading tends to be improved. Furthermore, when the amount is less than this upper limit, the liquid permeability under loading becomes more excellent and at the same time the mechanical strength of the water absorbing agent increases further.

The water-insoluble spherical single particles (d) may be mixed either before polymerization or after polymerization of crosslinked polymer.

(i) When (d) is mixed before polymerization, (d) is added into vinyl monomer (a1), (a2), (a3), crosslinking agent (b) and/or reaction solvent, then these are polymerized and crosslinked polymer in which (d) is dispersed is obtained.

(ii) When the water-insoluble spherical single particle (d) mixed after polymerization, (ii-i) (d) is added to the water-containing water absorbing agent and mixed to be treated to form into a mixture. In this case, since the water-insoluble spherical single particle (d) is mixed in a state of containing water, thereafter, when the water-containing crosslinked polymer is dried, a part of the water-insoluble spherical single particle (d) enters the crosslinked polymer, thus further improving gel water permeation speed. Furthermore, (ii-2) after the water-containing crosslinked polymer is dried, the water-insoluble spherical single particles (d) may be mixed. In this case, (d) is physically adsorbed to cover the particle surface of the crosslinked polymer or mixed as a simple mixture in which the crosslinked polymer and the spherical single particles are present separately. In this case, the phenomenon in which crosslinked polymers aggregate to each other via water can be prevented Furthermore, in the absorbed liquid including water insoluble part and water poor-soluble part, the phenomenon in which they coat the surface of the crosslinked polymer and deteriorates the performance can be prevented. This is thought to be the same as the principle in which a filter aid is used for preventing the clogging.

The methods (i), (ii-1) and (ii-2) may be used together. In these methods, (ii-2) is preferable.

The water-insoluble spherical single particle (d) may be added in any of the forms of powder, slurry, dispersion liquid, and emulsion liquid. Among these forms, it is preferable that the water-insoluble spherical single particles (d) are mixed with the crosslinked polymer in a state of single particles, that is, in a state, they are not aggregated. Particularly preferably, they are mixed in a state of dispersion liquid or emulsion liquid.

As a device for mixing the water-insoluble spherical single particle (d) into the water-containing crosslinked polymer, so that they are mixed uniformly, a conventionally known device may be used.

Examples of the known devices include a double arm type kneader, an internal mixer (Banbury mixer), a self-cleaning type mixer, a gear compounder, a screw type extruder, screw type kneader, a mincing machine, and the like. A plurality of these devices can be combined for using.

In the step <3> of the third invention, the standard deviation of the absorbance and the measurement method are the same as those in the step <2> of the second invention and the preferable range are also the same.

As a method for surface-crosslinking a crosslinked polymer with a surface crosslinking agent (b2), a conventional method, for example, a method including: mixing a solution containing the surface crosslinking agent (b2) and solvent with crosslinked polymer and subjecting it to heating reaction, can be employed.

When the crosslinked polymer is crosslinked on the surface with the surface crosslinking agnet (d2), a method of forming an ester bond or an amide bond, and making the standard deviation (S) of the absorbance analyzed by infrared absorption spectrophotometry of a carbonyl group or an amino group derived from an ester bond or an amide bond be 15 or less with respect to one particle of the crosslinked polymer includes, for example, (i) a method of continuously spraying the surface-cross linking agent (b2) to the surface of a crosslinking polymer particles; (ii) a method for continuously spraying a solution, an emulsified liquid, or a dispersing liquid including the surface-crosslinking agent (b2) to the surface of a crosslinking polymer particles; and (iii) a method of allowing a crosslinking polymer particles to flow in a fluidized bed and adding the surface-crosslinking agent (b2) or the solution, the emulsified liquid, or the dispersing liquid thereof.

As a solvent, water and organic solvent can be used.

When water is used, the amount of water is preferably 1 to 10 mass %, and more preferably 2 to 7 mass % based on the mass of the crosslinked polymer. That is to say, the upper limit of the amount of water to be used is preferably 10 mass %, and more preferably 7 mass %. Similarly, the lower limit is preferably 1 mass % and more preferably 2 mass %. When the amount is in this range, the permeation of the surface crosslinking agent (b2) into the inside of crosslinked polymer particles becomes sufficient, and the absorption amount under loading (X2) becomes more excellent.

As an organic solvent, conventionally known hydrophilic solvent can be used. Taken the permeation degree of the surface crosslinking agent (b2) permeating into the inside of the polymer particles, and reactivity of (b2) into account, the organic solvent can be selected appropriately. As a hydrophilic solvent, an alcohol having 1 to 6 carbon atoms and a ketone having 3 to 6 carbon atoms can be used. Examples of alcohol include methanol, ethanol, isopropyl alcohol, diethylene glycol and ethylene glycol monobutyl ether, and the like. Examples of ketone include acetone, methylethyl ketone and methylisobutyl ketone and the like. Among these, alcohol is preferable, methanol, ethanol, isopropyl alcohol and diethylene glycol are more preferable, and methanol and diethylene glycol are particularly preferable.

The solvent may be used singly or may be in combination of two kinds or more. Furthermore, both water and the organic solvent may be used.

The amount of solvent to be used can be varied depending upon the kinds of solvents, however, the amount is preferably 1 to 10 mass % based on the mass of the crosslinking polymer. Furthermore, the using ratio of organic solvent to water (organic solvent:water) can be varied arbitrarily based on the total mass of the water and organic solvent. For example the ratio is preferably 9:1, more preferably 7:3, particularly preferably 5:5, and the most preferably 3:7. When the ratio is in this range, the permeability of the surface crosslinking agent (b2) into the inside of a crosslinked polymer particle tends to be optimum, and as a result, the absorption amount under loading becomes excellent without reducing the water-retention amount.

The reaction temperature of the surface crosslinking reaction is preferably 80 to 200° C. and more preferably 100 to 160° C. Note here that the upper limit of the reaction temperature is preferably 200° C. and more preferably 160° C. Similarly, the lower limit is preferably 80° C. and more preferably 100° C. When the reaction temperature is in this range, the effective crosslinking reaction is carried out, less deterioration of the water-retension amount (X1) occurs and the absorption amount (X2) under loading is more excellent.

Furthermore, the reaction time can be varied depending upon the reaction temperature. The preferable reaction time is 3 to 60 minutes, more preferably 5 to 50 minutes, and particularly preferably 10 to 40 minutes. Note here that the upper limit of the reaction time is preferably 60 minutes, more preferably 50 minutes, and particularly preferably 40 minutes. Similarly, the lower limit of the reaction time is preferably 3 minutes, more preferably 5 minutes, and particularly preferably 10 minutes. When the reaction time is in this range, the crosslinking reaction is apt to be carried out effectively.

In this way, further additional surface crosslinking can be carried out to the crosslinked polymer obtained by the surface crosslinking reaction.

For the additional surface crosslinking, the same kind or different kinds surface crosslinking agent can be used.

For the polymerization method for the crosslinked polymer, conventionally known methods can be used. Examples of the polymerization methods include: a solution polymerization method using a polymerization initiator, an emulsion polymerization method, a suspension polymerization method, a reversed-phase suspension polymerization method, a thin film polymerization method, and a spraying polymerization method, and the like can be used.

As a method for controlling polymerization, an adiabatic polymerization method, a temperature control polymerization method, an isothermal polymerization method, and the like can be used.

When the suspension polymerization method or the reversed-phase suspension polymerization method is employed for the polymerization method, polymerization is carried out in the presence of a conventionally known dispersing agent, protective colloid, a surface active agent or a mixture of two or more of these materials if necessary. Furthermore, when the reversed-phase suspension polymerization method is used, a conventionally known solvent such as cyclohexane, normal hexane, normal heptane, toluene, xylene, etc, is used.

Among the polymerization methods, a solution polymerization method using a polymerization initiator is preferable. An aqueous solution polymerization method is particularly preferable, since organic solvent and the like, is not necessary to be used and it is advantageous in production cost.

The polymerization initiator is not particularly limited and a conventionally known one can be used. Examples of the polymerization initiator include (i) an azo type initiator, (ii) a peroxide based initiator, (iii) a redox type initiator, and (iv) an organic halide compound initiator, and the like.

(i) Examples of the azo type initiator include azobisisobutyronitrile, azobiscyano valeric acid and the salt thereof, 2,2'-azobis(2-amidinopropane)hydrochloride, and 2,2'-azobis(2-methyl-N-(2-hydroxyethyl)propionamide, and the like.

(ii) Examples of the peroxide type initiator include inorganic peroxide [for example, hydrogen peroxide, ammonium persulfate, potassium persulfate, and sodium persulfate, and the like], organic peroxide [for example, benzoyl peroxide, di-t-butyl peroxide, cumene hydroperoxide, succinic acid peroxide, and di(2-ethoxyethyl)peroxy dicarbonate, etc.]and the like.

(iii) The redox type initiator includes a combination of a reductant and an oxidizer. Examples of the reductant include sulfite or bisulfite of alkaline metal, ammonium sulfite, ammonium bisulfite, ferric chloride, ferric sulfate and ascorbic acid, and the like. Examples of the oxidizer include persulfate of alkaline metal, ammonium persulfate, hydrogen peroxide, and organic peroxide, and the like.

(iv) As the organic halide compound initiator, an organic halide compound having 1 to 10 or more halogen atoms and 1 to 15 or more carbon atoms and selected from the group consisting of alkyl halide, halogenated alkyl phenyl ketone, halogenated alkyl carboxylic acid, and halogenated alkyl carboxylic acid alkyl ester is used. Examples of the organic halide compound include, tetrachloromethane, trichlorobromomethane, trichloroiodomethane, dichloro methylphenyl ketone, 1-bromo-1-methylethylcarboxylic acid, 1-bromo-1-methylethylcarboxylic acid alkyl ester having alkyl group consisting of 1 to 8 carbon atoms (for example, methyl 1-bromo-1methylethylcarboxylate, ethyl 1-bromo-1methylethyl carboxylate, octyl 1-bromo-1-methylethyl carboxylate, and lauryl 1-bromo-1-methylethyl carboxylate) and the like.

Among them, (i) azo type initiator, (ii) peroxide type initiator, and (iii) redox type initiator are preferable. It is more preferable to use both (i) azo type initiator and (ii) peroxide initiator together with (iii) redox type initiator.

The amount of polymerization initiator to be used is preferably 0.005 to 0.5 mass %, more preferable 0.007 to 0.4 mass %, and particularly preferably 0.009 to 0.3 mass %, based on the total mass of the vinyl monomer (a1), (a2) and (a3) and internal crosslinking agent (b1). That is to say, the upper limit of the amount of polymerization initiator to be used is preferably 0.5 mass %, more preferably 0.4 mass % and particularly preferably 0.3 mass %. Similarly, the lower limit of the amount of polymerization initiator to be used is preferably 0.005 mass %, more preferably 0.007 mass % and particularly preferably 0.009 mass %.

The crosslinked polymer can be dried after crosshnked polymer is polymerized.

In the case of drying, the water content after drying is preferably 0 to 20 mass %, more preferably 0 to 10 mass %, particularly preferably 0 to 5 mass %, and the most preferably 0 to 2 mass % based on the mass of the crosslinked polymer. When the water content is in this range, handling property after drying (the powder fluidity of water absorbing agent particles, etc.) becomes further excellent.

Note here that the water content can be obtained by subtracting the amount after heating from the amount before heating. The heating is carried out by using an infrared water content measuring machine ("JE400" product by KETT Co.: 120±5° C., 30 minutes, atmospheric humidity before heating: 50±10% RH, lamp specification 100V, 40 W).

Examples of the drying method include usual methods, for example, a method using a heat air flow of the temperature of 80° C. to 230° C., a thin film drying method by using the drum dryer that was heated at 100° C. to 230° C., a heating) reduced drying method, a freeze drying method and a drying method using infrared ray, and the like.

Furthermore, the crosslinked polymer after drying can be pulverized.

When the crosslinked polymer is pulverized, mass-average particle size is preferably 100 to 800 μm, more preferably 200 to 500 μm, and particularly preferably 300 to 400 μm. That is to say, the upper limit of the mass-average particle size is preferably 800 μm, more preferably 500 μm, and particularly preferably 400 μm. Similarly, the lower limit of the mass-average particle size is preferably 100 μm, more preferably 200 μm, and particularly preferably 300 μm. When the mass-average particle size is in this range, the handling property (powder fluidity of water absorbing agent particle, etc.) after being pulverized becomes further excellent.

The mass-average particle size is calculated as follows. The particle size distributions of the crosslinked polymers are plotted on a logarithm probability paper in which the traverse axis shows particle size and the longitudinal axis shows content by mass. The diameter of particles occupying 50% with respect to the total particles is defined as the mass-average particle size.

Particle size distribution is measured as follows. Sieves respectively having an inner diameter of 150 mm, depth of 45 mm and openings of 710 μm, 500 μm, 300 μm, 149 μm and 106 μm are superposed on each other with the sieve having the largest openings at the top. 50 g of samples to be measured is placed on the sieve having the largest openings that is located at the top and subjected to sieving for 10 minutes by using a vibrating machine. The mass of samples to be measured remaining in each sieve is measured respectively and calculating the mass % of the samples with respect to the mass of the initial samples.

The smaller the content of fine particles is, the better the absorbing performance is. Preferably, the content of particles having the particles size of 100 μm or less is 3 mass % or less with respect to the total particles, and more preferably, the content of particles having the particles size of 150 μm or less is 3 mass % or less with respect to the total particles.

The content of the fine particles can be obtained by using a plot generated when the above-mentioned mass-average particle size is obtained.

The pulverizing method is not particularly limited, and usual device such as hammer pulverizing machine, shock pulverizing machine, rolling pulverizing machine, jet streaming pulverizing machine, etc. can be used.

The obtained pulverized product is classified with a sieve if necessary and the particle size is adjusted.

The shape of the crosslinked polymer particles is not particularly limited. Examples of the shape include indeterminate crushed shape, scale shape, pearl shape and rice grain shape, and the like. Among these shapes, indeterminate crushed shape is preferable because the shape easily can be entangled with fibrous products in an application for a paper diaper etc, and there is little possibility of the crosslinked polymer particles falling off.

The water content of the water absorbing agent of the present invention is preferably 1 to 12 mass %, more preferably 2 to 10 mass %, and particularly preferably 4 to 8 mass % from the viewpoint of the work efficiency, feeling, and moisture resistance, etc. when applied to the absorbent articles. That is to say, the upper limit of the water contents is preferably 12 mass %, more preferably 10 mass %, and particularly preferably 8 mass %. Similarly, the lower limit of the water content is preferably 1 mass %, more preferably 2 mass %, and particularly preferably 4 mass %. When the water content is in this range, particles of the water-absorbing agent is difficult to be destroyed due to the shock and it is easy to improve the workability.

Note here that the water content is not only determined by the drying step and can be adjusted through a surface crosslinking step and a water adding step. Furthermore, the water content can be measured from the amount reduced after drying process (120±5° C. for 30 minutes, etc) similar to the measuring method of water content mentioned above.

To the water absorbing agent of the present invention, additives can be added in any of the steps (before, during and after the polymerization of the crosslinked polymer) if necessary.

As the additives, surface active agents (anionic surface active agents, non-ionic surface active agents, cationic surface active agents and ampholytic surface active agents), antiseptic agents, fungicide, antibacterial agents, antioxidant, ultraviolet absorber, a coloring agent, flavoring agent, deodorizer and organic fibrous material, and the like can be used. Further, one or two ore more of the above-mentioned materials may be used.

Preferable examples of the surface active agent include the following agents.

Examples of the anionic surface active agent include ether carboxylic acid having 8 to 300 carbon atoms or salt thereof [polyoxyethylene (polymerization degree=1 to 100) lauryl ether sodium acetate, polyoxyethylene (polymerization degree=1 to 100) lauryl disodium sulfosuccinate, etc.], alkyl (ether)sulfuric ester salt having 8 to 300 carbon atoms [sodium lauryl sulfate, polyoxyethylene (polymerization degree=1 to 100) sodium lauryl sulfate, polyoxyethylene (polymerization degree=1 to 100) triethanolamine lauryl sulfate, polyoxyethylene (polymerization degree=1 to 100) coconut oil fatty acid monoethanol amide sodium sulfate], alkyl (or alkyl phenyl) sulfonic acid salt having 8 to 24 carbon atoms [sodium dodecylbenzene sulfonate, etc.], alkyl (ether)phosphate ester salt having 8 to 300 carbon atoms [lauryl sodium phosphate, polyoxyethylene (polymerization degree=1 to 100) lauryl ether sodium phosphate, etc.], fatty acid salt having 8 to 24 carbon atoms [sodium laurate, triethanolamine laurate, etc.], acylated amino acid salt [coconut oil fatty acid methyl taurine sodium, coconut oil fatty acid sarcosine sodium, coconut oil fatty acid saocosine triethanolamine, N-coconut oil fatty acid acyl-L-triethanolamine glutamate, N-coconut oil fatty acid acyl-L-sodium glutamate, lauroylmethyl-β-alanine sodium, etc.] and others [polyoxyethylene (polymerization degree=1 to 100) lauroyl ethanol amide disodium sulfosuccinate, etc.], and the like.

Furthermore, examples of the nonionic surface active agent include: aliphatic alcohol (the number of carbon atoms: 8 to 24) alkylene oxide (the number of carbon atoms: 2 to 8) adduct (polymerization degree=1 to 100) [lauryl alcohol ethylene oxide adduct (polymerization degree=20), oleyl alcohol ethylene oxide adduct (polymerization degree=10), sperm alcohol ethylene oxide adduct (polymerization degree=35), etc.], polyoxy alkylene (the number of carbon atoms: 2 to 8, polymerization degree=1 to 100) higher fatty acid (the number of carbon atoms: 8 to 24) ester [polyethylene glycol monostearate (polymerization degree=20), polyethylene glycol distearate (polymerization degree=30), etc.], polyvalent (the number of valences: 2 to 10 or more) alcohol fatty acid (the number of carbon atoms: 8 to 24) ester [glycerine monostearate, ethyleneglycol monostearate, sorbitan lauric acid(mono/di)ester, sorbitan palmitin acid(mono/di)ester, sorbitan stearic acid(mono/di) ester, sorbitan oleic acid(mono/di)ester, sorbitan coconut oil(mono/di) ester, etc.], polyoxyalkylene (the number of carbon atoms: 2 to 8, polymerization degree=1 to 100) polyvalent (the number of valences: 2 to 10 or more) alcohol higher fatty acid (the number of carbon atoms: 8 to 24) ester[polyoxyethylene (polymerization degree=10) sorbitan lauric acid(mono/di)ester, polyoxyethylene (polymerization degree=20) sorbitan palmitin acid(mono/di)ester, polyoxyethylene (polymerization degree=15) sorbitan stearic acid (mono/di)ester, polyoxyethylene (polymerization degree=10) sorbitan oleic acid(mono/di)ester, polyoxyethylene (polymerization degree=25) lauric acid(mono/di)ester, polyoxyethylene (polymerization degree=50) stearic acid (mono/di)ester, polyoxyethylene (polymerization degree=18) oleic acid(mono/di)ester, sorbitan, polyoxyethylene (polymerization degree=50) dioleic acid methyl glucoside, etc.] fatty acid alkanol amide [1:1 type coconut oil fatty acid diethanol amide, 1:1 type lauric acid diethanol amide, etc.], polyoxy alkylene (the number of carbon atoms: 2 to 8, polymerization degree=1 to 100) alkyl (the number of carbon atoms: 1 to 22) phenyl ether(polyoxyethylene (polymerization degree=20) nonyl phenyl ether etc.), polyoxy alkylene (the number of carbon atoms: 2 to 8, polymerization degree=1 to 100) alkyl (the number of carbon atoms: 8 to 24) amino ether, alkyl (the number of carbon atoms: 8 to 24) dialkyl (the number of carbon atoms: 1 to 6) amine oxide[lauryl dimethylamine oxide, etc.], polydimethyl siloxane polyoxyethylene adduct and polyoxy ethylene-polyoxypropylene block polymer (weight-average molecular weight=150 to 10000), and th like. Note here that in the above, ". . . (mono/di)ester" means ". . . monoester" or ". . . diester".

Furthermore, examples of the cationic surface active agent include: quaternary ammonium salt [stearyl trimethylammonium chloride, biphenyl trimethylammonium chloride, distearyl dimethylammonium chloride, ethyl sulfuric acid lanolin fatty acid amino propylethyl dimethylammonium, etc] and amine salt [diethyl aminoethyl stearyl amide lactate, dilauryl amine hydro chloride, oleylamine lactate, etc.] and the like.

Furthermore, examples of the ampholytic surface active agent include: betaine type ampholytic surface active agent [coconut oil fatty acid amidopropyl dimethyl aminoacetic acid betaine, lauryl dimethyl aminoacetic acid betaine, 2-alkyl N-carboxy methyl-N-hydroxyethyl imidazolinium betaine, lauryl hydroxysulfo betaine, lauroyl amideethyl hydroxyethyl carboxymethyl betaine hydroxypropyl sodium phosphorate, etc.], amino acid type ampholytic surface active agent [sodium β-lauryl aminopropionate, etc.] and the like.

Examples of antiseptics include, for example, preservative such as salicyl acid, sorbic acid, dehydroacetic acid, methyl naphthoquinone, etc., and sterilizer such as chloramines B, nitrofurazone, etc., and the like.

Examples of fungicide include, for example, butyl p-oxybenzoate, and the like.

Examples of antibacterial agent include, for example, benzalkonium chloride salt, chlorhexidine gluconate, and the like.

Examples of antioxidant include, for example, hindered phenol type antioxidant such as triethyleneglycol bis-[3-(3-t-butyl 5-methyl-4-hydroxyphenyl) propionate], 1,6-hexanediol-bis[3-(3,5-di-t-butyl-4-hydroxyphenyl)propionate], octadecyl-3-(3,5-di-t-butyl-4-hydroxyphenyl propionate, 3,5-di-t-butyl-4-hydroxybenzyl phosphonate-diethyl ester, etc.; amine type antioxidant such as n-butyl amine, triethyl amine, diethyl aminomethyl methacrylate, etc., and the like.

Examples of ultraviolet absorber include, for example, benzotriazole type ultraviolet absorber such as 2-(5-methyl-2-hydroxyphenyl)benzotriazole, 2-(3, 5-di-t-butyl-2-hydroxyphenyl)benzotriazole, 2-(3,5-di-t-butyl-2-hydroxyphenyl)-5-chloro-benzotriazole, 2-(3, 5-di-t-amyl-2-hydroxyphenyl)benzotriazole; triazine type ultraviolet absorber such as 2-(4, 6-diphenyl-1,3,5-triazine-2-yl)-5-[hexyl)oxy]-phenol, etc.; benzophenone type ultraviolet absorber such as 2-hydroxy-4-n-octyloxybenzophenone, and the like; oxalic acid anilide type ultraviolet absorber such as 2-ethoxy-2'-ethyl oxalic acid bisanilide, and the like.

Examples of coloring agent include, for example, an inorganic pigment such as titanium oxide, ferrite, etc.; an organic pigment such as azolake type, benzimidazolone type, phthalocyanine type, etc. dyes such as nigrosine type, aniline type, etc., and the like.

Examples of flavoring agent include, for example, natural perfume such as musk, abies oil, turpentine oil, etc.; synthetic perfume such as menthol, citral, p-methyl acetophenone, floral, etc., and the like.

Examples of deodorizer include, for example, zeolite, silica, flavonoid, cyclodextrin, etc.

Examples of organic fibrous material include, for example, natural fiber [cellulose base natural fiber (cotton, sawdust, straw, etc.) and others, grass peat, wool, microfibril, bacterial cellulose, etc.], artificial fiber rayon, cellulose with acetate, etc.), synthetic fiber (polyamide, polyester, acryl, etc.), pulp [kraft pulp, mechanical pulp (ground pulp from log, ground pulp by Asplund process, etc.), chemical pulp (sulphite pulp, soda pulp, sulphate pulp, nitrate pulp, chlorine pulp, etc.), semichemial pulp, recycled pulp (or example, mechanically broken or crushed material of paper made of pulp, and recycled waste-paper pulp that is a mechanically broken or crushed waste paper, etc.) and the like.

When such additives are added, the adding amount differs depending upon applications of use, however, the based on the mass of the water absorbing agent, the amount is preferably $10^{-6}$ to 20 mass %; further preferably $10^{-5}$ to 10 mass %; and particularly preferably $10^{-4}$ to 5 mass %. That is to say, the upper limit of the adding amount is preferably 20 mass %, further preferably 10 mass %, and particularly preferably 5 mass %. Similarly, the lower limit is preferably $10^{-6}$ mass %, further preferably $10^{-5}$ mass %; and particularly preferably $10^{-4}$ mass %. In this range, antimicrobial activity etc. can be provided without lowering the absorbing performance of the water absorbing agent.

The water absorbing agent of the present invention is significantly excellent in the balance in the water-retention amount (x1), absorption amount under loading (x2) and water permeation speed under loading (Y). When the water absorbing agent of the present invention is applied to various kinds of absorbers, absorbing articles excellent in the absorbing performance can be obtained.

For example, a method for applying the water absorbing agent to the absorber includes, applying water absorbing agent and fibrous material. Examples of the method include: (1) a method of dispersing particles of the water-absorbing agent to between layers of fibrous materials made of pulp, etc. disposed in a layered structure; (2) a method of mixing a fibrous material including pulp, thermal melting fibers, etc. and particles of the water absorbing agent; and (3) a method for sandwiching the water absorbing agent particles if necessary, together with the fibrous material by two or more water absorption paper or non-woven fabrics, and the like.

Fibrous materials, which have been conventionally used for absorbent articles (for example, various kinds of fluff pulp, cotton pulp, etc.) are used, and raw materials of the fibrous materials (needle-leaved tree, broad-leaved tree) etc. and the production method [chemical pulp, semichemical pulp, chemithermo-mechanical pulp (CTMP), etc.], bleaching method, etc. are not particularly limited. Furthermore, examples of fibrous materials include, in addition to the above-mentioned organic fibrous material, if necessary, a synthetic fiber that is not swollen with water that also can be used singly or together with the above-mentioned fluff pulp or cotton pulp, etc. Examples of the synthetic fiber include polyolefin fiber (for example, polyethylene fiber, polypropylene fiber, etc.), polyester fiber (for example, polyethylene terephthalate fiber, etc.), polyolefin-polyester conjugated fiber, polyamide fiber, polyacrylonitrile fiber, and the like.

The length and thickness of the fibrous material are not particularly limited. In general, the length is suitably 1 to 200 mm and the fineness is suitably 1 to 100 denir (0.11 to 110 detex).

The shape is not particularly limited as long as it has a fibrous shape. Examples of the shape of the fiber include web, thin cylinder, cut split yarn, staple, filament, and the like.

The adding amount of the water absorbing agent of the present invention with respect to the absorber can be altered depending upon the kinds or size of the absorbers, targeted absorbing performance. However, the amount is preferably 30 to 95 mass %, furthermore 40 to 94 mass %, and particularly preferably 50 to 95 mass % based on the total mass of the water absorbing agent and fibrous material. When the amount is in this range, the absorbing performance of the obtained absorbers can be apt to be more excellent.

Since the water absorbing agent of the present invention can provide a dry feeling even if it absorbs absorbed liquid (body fluid such as sweat, urine, and blood, etc. as well as water such as seawater, underground water, and muddy water, etc.), when the water absorbing agent is applied to hygienic products such as disposable diapers, sanitary napkin, etc., not only excellent absorbing performance but also an excellent property in preventing absorbed liquid from returning easily under pressure can be observed.

Therefore, by using the water absorbing agent of the present invention, it is possible to manufacture absorbent articles exerting high absorbing performance in any states easily.

That is to say, even in the case where the absorbing articles are in a state under loading, for example, where a user sits down or lies down, the absorption amount and the absorption speed are not deteriorated. As a result, the problems such as leakage and the like hardly occur.

As an absorbent article, an absorbent article including an absorber, a liquid permeation sheet, and an air permeation back sheet is preferable. More preferable example is an absorbent article as a hygienic article.

Examples of hygienic articles include, for example, disposable diapers (disposable diapers for children, disposable diapers for adult, etc.), napkin (sanitary napkin, and the like), paper towel, pads (incontinence pads, under pads for surgical operations, etc.), pet sheets (pet urine absorption sheet), and the like. Among these hygienic products, disposable diapers are more suitable. Furthermore, among disposable diapers, disposable diapers having the surface dryness value measured by the following SDME method of 50% or more, more preferably 55% or more are more suitable.

Surface Dryness Value by SDME Method

The surface dryness value by SDME method was measured in the following procedure by using a SDME (Surface Dryness Measurement Equipment) tester (product of WK System Co.).

The detector of the SDME tester is placed on a sufficiently wetted disposable diaper (the disposable diaper had been soaked sufficiently in artificial urine (0.03 mass % of calcium chloride, 0.08 mass % of magnesium sulphate, 0.8 mass % of sodium chloride, and 99.09 mass % of deionized water) in an amount of covering disposable diaper and allowed to stand still for 60 minutes) for setting 0% dryness value. Then, the detector of the SDME tester is placed on a dry disposable diaper (disposable diaper was heated and dried at 8° C. for 2 hours) for setting 100% dryness. Thus, the adjustment of the SDME tester is carried out.

Next, a metallic ring (inner diameter: 70 mm, outer diameter: 80 mm, length: 50 mm, and weight: 300 g) is set in the center of a disposable diaper to be measured and 80 ml of artificial urine is poured. Immediately after pouring, the metallic ring was removed and the SDME detector is set in contact with the disposable diaper in the center of the disposable diaper and measurement is started. 5 minutes after the measurement is started, the measurement value is defined as a surface dryness value by the SDME.

Note here that the water absorbing agent of the present invention is useful not only for the use of application for the above-mentioned hygienic products but also for the purpose of various applications such as a pet urine absorbing agent, a urine gelling agent for portable toilet, a freshness retaining agent for vegetable, a drip absorbing agent for meat and fish, a cold retaining material, a disposable pocket warmer, a gelling agent for batteries, a water retention material for plants and soil, etc., an anti-dewing material, a water sealing agent, or a packing agent, artificial snow, etc.

Hereinafter, the present invention will be described in more detail by way of Examples and Comparative Examples. However, the present invention is not necessarily limited thereto. Hereinafter, part means parts by mass and % means mass % unless otherwise specified.

Note here that the water-retention amount (x1), an absorption amount under loading (x2), liquid permeation speed under loading (Y), particle distribution and a mass-average particle size were measured by the above-mentioned method, respectively.

EXAMPLE 1

77 parts of sodium acrylate, 22.85 parts of acrylic acid, 0.15 parts of N,N'-methylene bisacrylamide, 293 parts of deionized water, and 0.001 parts of dichlorotris(triphenylphosphine)ruthenium were placed in a glass reaction container and the contents were maintained at 3° C. while stirring and mixing.

After introducing nitrogen into the contents so as to make the dissolved oxygen content 1 ppm or less, 0.3 parts of 1% aqueous solution of hydrogen peroxide, 0.8 parts of 0.2% aqueous solution of ascorbic acid, and 0.8 parts of 2% aqueous solution of 2,2'-azobisamidinopropane dihydrochloride were added and mixed for initializing the polymerization. A hydrogel polymer (A-1) was obtained after the polymerization was carried out at the temperature of 80±2° C. for about 5 hours.

This hydrogel polymer (A-1) was chopped by an internal mixer and then dried in a through-flow band type drier under the conditions of a temperature of 135° C. and a wind speed of 2.0 m/sec so as to obtain a dry polymer.

This dry polymer was pulverized by using a commercially available juicer mixer, and the particle size was adjusted to 30 to 60-mesh particle size by using sieves with 590 μm and 250 μm mesh openings, 100 parts of which were stirred at high speed (by using "High-speed stirring turbulizer" (product of Hosokawa Micron Co.): number of revolution; 2000 rpm) while adding by spraying 2 parts of 10% water/methanol mixing solution of ethylene glycol diglycidyl ether (mass ratio of water/methanol=70/30) to be mixed. The mixture was allowed to stand at 140° C. for 30 minutes to be crosslinked by the heating, and thereby a water absorbing agent (1) was obtained.

The particle size distribution, the standard deviation of the absorbance by infrared absorption spectrophotometry and evaluation results with respect to the water absorbing agent (1) are shown in Table 1.

EXAMPLE 2

81.7 parts of acrylic acid, 0.15 parts of N,N'-methylene bisacrylamide, 241 parts of deionized water, and 0.001 parts of dichlorotris(triphenylphosphine)ruthenium were placed in a glass reaction container and the contents were maintained at 3° C. while stirring and mixing.

After introducing nitrogen into the contents so as to make the dissolved oxygen content 1 ppm or less, 0.3 parts of 1% aqueous solution of hydrogen peroxide, 0.8 parts of 0.2% aqueous solution of ascorbic acid, and 0.8 parts of 2% aqueous solution of 2,2'-azobisamidinopropane dihydrochloride were added and mixed for initializing the polymerization. A hydrogel polymer was obtained after the polymerization at the temperature of 80±2° C. for about 5 hours.

This hydrogel polymer was chopped and kneaded in an internal mixer by adding 109.1 parts of 30% aqueous solution of sodium hydroxide so as to obtain a hydrogel (A-2) in which 72 mol % of carboxyl group was neutralized.

This hydrogel polymer (A-2) was dried in a through-flow band type drier under the conditions of a temperature of 140° C. and a wind speed of 2.0 m/sec.

The obtained dry polymer was pulverized by using a commercially available juicer mixer and the particle size was adjusted to 30 to 60-mesh particle size by using sieves with 590 μm and 250 μm mesh openings, 100 parts of which were stirred at high speed (by using "High-speed stirring turbulizer" (product of Hosokawa Micron Co.): number of revolution; 2000 rpm) while adding by spraying 2 parts of 10% water/methanol mixing solution of ethylene glycol diglycidyl ether (mass ratio of water/methanol=70/30) to be mixed. The mixture was allowed to stand at 140° C. for 30 minutes to be crosslinked by the heating. Furthermore, one part of "KLEBOSOL 30CAL25" (B1) produced by Clariant Japan Corp. (30% aqueous dispersion solution, pH=3.5, average particle diameter=25 nm, specific surface area=120 $m^2/g$, solid contents=30%) that is a colloidal aqueous solution of spherical silicon oxide was added, and thereby the water absorbing agent (2) was obtained.

The particle size distribution, the standard deviation of the absorbance by infrared absorption spectrophotometry and evaluation results with respect to the water absorbing agent (2) are shown in Table 1.

EXAMPLE 3

77 parts of sodium acrylate, 22.6 parts of acrylic acid, 0.4 parts of pentaerythritol triallyl ether and 293 parts of deionized water were placed in a glass reaction container and the contents were maintained at 3° C. while stirring and mixing.

After introducing nitrogen into the contents so as to make the dissolved oxygen content 1 ppm or less, 0.3 parts of 1% aqueous solution of hydrogen peroxide, 0.8 parts of 0.2% aqueous solution of ascorbic acid, and 0.8 parts of 2% aqueous solution of 2,2'-azobisamidinopropane dihydrochloride were added and mixed for initializing the polymerization. The polymerization was carried out at a temperature of 55±2° C. for about 8 hours so as to obtain a hydrogel polymer (A-3).

This obtained (A-3) was chopped by using an internal mixer and then dried in a through-flow band type drier under the conditions of a temperature of 135° C. and a wind speed of 2.0 m/sec.

This obtained dry product was pulverized in a commercially available juicer mixer and the particle size was adjusted to 30 to 60-mesh particle size by using sieves with 590 μm and 250 μm mesh openings, 100 parts of which were stirred at high speed (by using "High-speed stirring turbulizer" (product by Hosokawa Micron Co.): number of revolution; 2000 rpm) while adding by spraying 2 parts of 10% water/methanol mixing solution of ethylene glycol diglycidyl ether (mass ratio of water/methanol=70/30) by using a two-fluid type spray nozzle to be mixed. The mixture was heated to be crosslinked at 140° C. for 30 minutes. Furthermore, similar to Example 2, 1 part of (B1) was added, and thereby a water absorbing agent (3) was obtained.

The particle size distribution, the standard deviation of the absorbance by infrared absorption spectrophotometry and evaluation results with respect to the water absorbing agent (3) are shown in Table 1.

EXAMPLE 4

81.7 parts of acrylic acid, 0.4 parts of pentaerytlritol triallyl ether, 241 parts of deionized water, and 0.001 parts of dichlorotris(triphenylphosphine)ruthenium were placed in a glass reaction container and the contents were maintained at 3° C. while stirring and mixing.

After introducing nitrogen into the contents so as to make the dissolved oxygen content 1 ppm or less, 0.3 parts of 1% aqueous solution of hydrogen peroxide, 0.8 parts of 0.2% aqueous solution of ascorbic acid, and 0.8 parts of 2% aqueous solution of 2,2'-azobisarnidinopropane dihydrochloride were added and mixed for initializing the polymerization. The polymerization was carried out at a temperature of 80±2° C. for about 5 hours so as to obtain a hydrogel polymer.

This hydrogel polymer was chopped and kneaded in an internal mixer by adding 109.1 parts of 30% aqueous solution of sodium hydroxide so as to obtain a hydrogel (A-4) in which 72 mol% of carboxyl group was neutralized.

Furthermore, this hydrogel (A-4) was dried in a through-flow band type drier under the conditions of a temperature of 140° C. and a wind speed of 2.0 m/sec.

The obtained dry product was pulverized by using a commercially available juicer mixer and the particle size was adjusted to 30 to 60-mesh particle size by using sieves with 590 μm and 250 μm mesh openings, 100 parts of which were stirred at high speed (by using "High-speed stirring turbulizer" (product by Hosokawa Micron Co.): number of revolution; 2000 rpm) while adding by spraying 2 parts of 10% water/methanol mixing solution of ethylene glycol diglycidyl ether (mass ratio of water/methanol=70/30) by using a two-fluid type spray nozzle to be mixed. The mixture was allowed to stand at 140° C. for 30 minutes to be crosslinked by the heating. Furthermore, similar to Example 2, one part of (B1) was added so as to obtain a water absorbing agent (4) was obtained.

The particle size distribution, the standard deviation of the absorbance by infrared absorption spectrophotometry and evaluation results with respect to the water absorbing agent (4) are shown in Table 1.

EXAMPLE 5

A surface-crosslinked absorbing agent (5) was obtained by the same method as in Example 1 except that instead of 0.15 parts of N,N'-methylene bisacrylamide, 0.17 parts of ethylene glycol diglycidyl ether was used.

The particle size distribution, the standard deviation of the absorbance by infrared absorption spectrophotometry and evaluation results with respect to the water absorbing agent (5) are shown in Table 1.

EXAMPLE 6

A surface-crosslinked absorbing agent (6) was obtained by the same method as in Example 2 except that instead of 0.3 parts of 1% aqueous solution of hydrogen peroxide, 0.3 parts of 1% aqueous solution of potassium persulfate was used.

The particle size distribution, the standard deviation of the absorbance by infrared absorption spectrophotometry and evaluation results with respect to the water absorbing agent (6) are shown in Table 1.

EXAMPLE 7

A surface cross-linked absorbing agent (7) was obtained by the same method as in Example 4 except that 0.5 parts of pentaerydiritol triallyl ether was used instead of 0.4 parts of pentaerythritol triallyl ether; 375 parts of deionized water was used instead of 241 parts of deionized water; and 1.0 parts of 2% aqueous solution of 2,2'-azobisamidinopropane dihydrochloride was used instead of 0.8 parts of 2% aqueous solution of 2,2'-azobisamidinopropane dihydroclloride.

The particle size distribution, the standard deviation of the absorbance by infrared absorption spectrophotometry and evaluation results with respect to the water absorbing agent (7) are shown in Table 1.

EXAMPLE 8

A surface cross-linked absorbing agent (8) was obtained by the same method as in Example 4 except that instead of (B1), the following spherical single-particle (B2) mentioned below was used. The particle size distribution, the standard deviation of the absorbance by infrared absorption spectrophotometry and evaluation results with respect to the water absorbing agent (8) are shown in Table 1.

(B2)="KLEBOSOL 30CAL50" produced by Clariant Japan Corp. (30% aqueous dispersion solution, pH=3.9, average particle diameter=50 nm, specific surface area=50 $m^2/g$)

EXAMPLE 9

121.2 parts of cyclohexane was placed in a four-necked round-bottom flask equipped with a stirrer, a reflux condenser, a thermometer and an introduction tube for nitrogen gas, followed by adding 0.9 parts of sorbitan monostearate so as to be dissolved. Thereafter, a nitrogen gas flow was provided so as to purge dissolved oxygen. Separately, 70.0 parts of 25% aqueous solution of sodium hydroxide was added in a mixture solution of 45 parts of acrylic acid and 6.4 parts of water in a conical beaker under cooling on ice, thereby neutralizing 70 mol % of caroboxyl group. Then, 0.033 parts of N,N'-methylene bisacrylamide as a crosslinking agent, 0.0546 parts of sodium hypophosphite as a aqueous chain transfer agent, and 0.031 parts of 2,2'-azobisamidinopropane dihydrochloride as a polymerization initiator were added to be dissolved.

Then, the contents contained in the conical beaker were added into the contents contained in the above-mentioned four-necked round bottom flask while stirring and dispersing. The temperature inside the flask was increased while bubbling nitrogen gas in an oil bath, the internal temperature thereof was maintained at 60±2° C. and polymerization was carried out while stirring for 2 hours. The contents after two hours had a slurry state in which a crosslinked polymer that was swollen with water was dispersed in cyclohexane. Then, the temperature of the oil bath was increased so as to dewater the swollen crosslinked polymer so that the moisture content thereof became 20% by azeotropy with cyclohexane in the flask. The stirring was stopped after being dewatered. Since wet polymer particles were sedimented in the bottom of the round-bottom flask, they could easily be separated from the cyclohexane phase by decantation. The separated wet polymer was transferred to a vacuum drier, heated to 80 to 90° C., and attached cyclohexane and water were removed. As a result, fine and dry crosslinked polymer particulate materials were obtained. 30 parts of the obtained materials were stirred at high speed (by using "High-speed stirring turbulizer" (product by Hosokawa Micron Co.): number of revolution; 2000 rpm) while adding by spraying 0.6 parts of 10% water/methanol miig solution of ethylene glycol diglycidyl ether (mass ratio of water/methanol=70/30) by using a two-fluid type spray nozzle to be mixed. The mixture was heated to be crosslinked at 140° C. for 30 minutes. Furthermore, similar to Example 2, 1 part of (B1) was added, and thereby a water absorbing agent (9) was obtained.

The particle size distribution, the standard deviation of the absorbance by infrared absorption spectrophotometry and evaluation results with respect to the water absorbing agent (3) are shown in Table 1.

EXAMPLE 10

An absorbing agent (10) was obtained by the same method as in Example 4 except that instead of the mass ratio of water/methanol=70/30 as a solvent composition at the time of surface crosslink, the mass ratio of 98/2 was employed.

The particle size distribution, the standard deviation of the absorbance by infrared absorption spectrophotometry and evaluation results with respect to the water absorbing agent (10) are shown in Table 1.

EXAMPLE 11

An absorbing agent (11) was obtained by the same method as in Example 1 except that the polymerization was carried out at a temperature of 55±2° C. for 8 hours instead of being polymerized at a temperature of 80±2° C. for 5 hours. The particle size distribution, the standard deviation of the absorbance by infrared absorption spectrophotometry and evaluation results with respect to the water absorbing agent (11) are shown in Table 1.

EXAMPLE 12

An absorbing agent (12) was obtained by the same method as in Example 2 except that the polymerization was carried out at a temperature of 55±2° C. for 8 hours instead of being polymerized at a temperature of 80±2° C. for 5 hours. The particle size distribution, the standard deviation of the absorbance by infrared absorption spectrophotometry and evaluation results with respect to the water absorbing agent (12) are shown in Table 1.

COMPARATIVE EXAMPLE 1

A comparative water absorbing agent (1') was obtained by the same method as in Example 1 except that dichlorotris(triphenylphosphine)ruthenium was not used. The particle size distribution, the standard deviation of the absorbance by infrared absorption spectrophotometry and evaluation results with respect to the comparative water absorbing agent (1') are shown in Table 1.

COMPARATIVE EXAMPLE 2

A comparative water absorbing agent (2') was obtained by the same method as in Example 2 except that dichlorotris(triphenylphosphine)ruthenium was not used; and instead of the mass ratio of water/methanol=70/30 as a solvent composition at the time of surface crosslink, the mass ratio of 98/2 was employed. The particle size distribution, the standard deviation of the absorbance by infrared absorption spectrophotometry and evaluation results with respect to the comparative water absorbing agent (2') are shown in Table 1.

COMPARATIVE EXAMPLE 3

A comparative water absorbing agent (3') was obtained by the same method as in Example 1 except that instead of the mass ratio of water/methanol=70/30 as a solvent composition at the time of surface crosslink, the mass ratio of 98/2 was employed. The particle size distribution, the standard deviation of the absorbance by infrared absorption spectrophotometry and evaluation results with respect to the comparative water absorbing agent (3') are shown in Table 1.

(that is, 10 minutes later from the first pouring) 80 ml of third artificial urine was poured and allowed to stand still for 5 minutes.

The load and the acrylic plate were removed and artificial urine that was not absorbed was removed. Thereafter, the

TABLE 1

|  |  | Example |  |  |  |  |  |  |  |  |  |  |  | Comparative Example |  |  |
|---|---|---|---|---|---|---|---|---|---|---|---|---|---|---|---|---|
|  |  | 1 | 2 | 3 | 4 | 5 | 6 | 7 | 8 | 9 | 10 | 11 | 12 | 1 | 2 | 3 |
|  | Ab | (1) | (2) | (3) | (4) | (5) | (6) | (7) | (8) | (9) | (10) | (11) | (12) | (1') | (2') | (3') |
| P | I | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| (%) | II | 9.3 | 14.9 | 19.3 | 18.1 | 15.2 | 14.8 | 18.1 | 9.3 | 19.3 | 18.3 | 9.2 | 14.8 | 15.2 | 18.1 | 9.4 |
|  | III | 56.6 | 56.6 | 57.5 | 55.3 | 56.4 | 56.7 | 55.3 | 56.6 | 57.5 | 56.1 | 56.1 | 56.4 | 56.4 | 55.3 | 56.8 |
|  | IV | 22.4 | 26.6 | 22.0 | 22.4 | 26.5 | 26.5 | 22.4 | 22.4 | 22.0 | 21.9 | 22.3 | 26.8 | 26.5 | 22.4 | 22.2 |
|  | V | 1.6 | 1.8 | 1.1 | 2.1 | 1.8 | 1.9 | 2.1 | 1.6 | 1.1 | 2.0 | 2.2 | 2.1 | 1.8 | 2.1 | 1.5 |
| Average particle size (μm) |  | 363 | 365 | 362 | 354 | 364 | 363 | 354 | 363 | 362 | 363 | 364 | 366 | 364 | 354 | 354 |
| Standard deviation of absorbance |  | 2 | 2 | 2 | 2 | 2 | 2 | 2 | 2 | 2 | 15 | 2 | 2 | 2 | 15 | 15 |
| Water retention amount (×1) (g/g) |  | 36 | 36 | 35 | 35 | 35 | 35 | 36 | 36 | 35 | 35 | 36 | 36 | 34 | 34 | 35 |
| Absorption amount under loading (×2) (g/g) |  | 26 | 23 | 22 | 25 | 26 | 23 | 26 | 24 | 23 | 23 | 26 | 23 | 20 | 18 | 19 |
| Liquid permeation speed (Y) (ml/min) |  | 2 | 7 | 9 | 20 | 2 | 7 | 20 | 18 | 18 | 17 | 2 | 7 | 1 | 16 | 1 |

P (%): particle size
Ab: water absorbing agent
I: 710 μm or more
II: 710-500 μm
III: 500-298 μm
IV: 298-149 μm
V: less than 149 μm Evaluation of Disposable Diaper Absorbers were produced by using the water-absorbing agents (1) to (12) of the present invention and comparative absorbing agents (1') to (3'). Disposable diaper produced by the below-mentioned method was examined for the absorption amount under loading, absorbing speed under loading, diffusion area under loading, surface dryness, and surface dryness value by SDME. Hereinafter, % means mass % unless otherwise specified. The evaluation results are shown in Table 2.

Absorption Amount of Diaper Under Loading

An instrument including an acrylic plate (140 mm×360 mm, and 0.5 Kg in mass) having a cylindrical tube (3 cm in inside diameter, and 20 cm in length) placed in a central portion thereof and provided with a hole having the same inner diameter as that of the cylindrical tube in the central portion was prepared. The acrylic plate was placed on a diaper (140 mm×360 mm), which was placed horizontally, with the face that does not have a cylindrical tube downward. Load of 20 Kg was applied to the acrylic plate uniformly (total loading: 20.5 Kg). Then, 80 ml of artificial urine was poured in the cylindrical tube, and 5 minutes later, 80 ml of second artificial urine was poured. 5 minutes later mass (Wg) of this disposable diaper (wet sample) was measured. W denotes an absorption amount under loading of diaper.

Absorption Rate Under Loading

An instrument including an acrylic plate (140 mm×360 mm, and 0.5 Kg in mass) having a cylindrical tube (3 cm in inside diameter, and 20 cm in length) placed in a central portion thereof and provided with a hole having the same inner diameter as that of the cylindrical tube in the central portion was prepared. The acrylic plate was placed on a diaper (140 mm×360 mm), which was placed horizontally, with the face that does not have a cylindrical tube downward. Load of 20 Kg was applied to the acrylic plate uniformly (total loading: 20.5 Kg). Then, 80 ml of artificial urine (colored with blue ink) was poured in the cylindrical tube, and 10 minutes later, a second 80 ml artificial urine was poured. Similarly, 10 minutes later, a third 80 ml of artificial urine was poured.

The period of time (second) from the time at which the third colored artificial urine was poured to the time the third artificial urine was absorbed by a disposable diaper so as to empty the cylindrical tube was measured and the time was defined as an absorption speed under loading.

Diffusion Area Under Loading

After measuring the absorption speed under loading of a disposable diaper, by using the disposable diaper, the area of the absorbed synthetic urine horizontally spread was measured and defined as the diffusion area.

Surface Dryness

After measuring the diffusion area under loading, by using the disposable diaper, the dry feeling of the diaper surface was judged by finger toughing of 10 panelists with the below-mentioned four criteria. The average of the 10 panelists was determined and defined as the surface dryness.

○: Excellent dry feeling
Δ: Dry feeling at a satisfactory level with slight wetting
X: Wetting state with poor dry feeling or wet state without dry feeling Surface Dryness Value by SDME Method The surface dryness value by SDME method was measured in the following procedure by using a SDME (Surface Dryness Measurement Equipment) tester (product of WK System Co.).

The detector of the SDME tester was placed on a sufficiently wetted disposable diaper (the disposable diaper had been soaked sufficiently in artificial urine and allowed to stand still for 60 minutes) for setting 0% dryness value. Then, the detector of the SDME tester was placed on a dry disposable diaper (disposable diaper was heated and dried at 8° C. for 2 hours) for setting 100% dryness. Thus, the adjustment of the SDME tester was carried out.

Next, a metallic ring (inner diameter: 70 mm, length: 50 mm) was set in the center of a disposable diaper to be measured and 80 ml of artificial urine was poured. Immediately after pouring, the metallic ring was removed and the SDME detector was set in contact with the disposable diaper in the center of the disposable diaper and measurement was started. 5 minutes after the measurement was started, the measurement value was defined as a surface dryness value by the SDME.

EXAMPLES 13 TO 24

A mixture obtained by mixing 100 parts of fluff pulp and 100 parts of one of the water absorbing agents (1) to (12) obtained in Examples 1 to 12 of the present invention by using an air blender was evenly piled so as to have the basic weight (mass per unit area) of about 400 g/m², and pressed with the pressure of 5 Kg/cm² for 30 seconds to obtain absorbers (B1) to (B12) of Examples 13 to 24. The obtained absorber was cut into a rectangular shape of 14 cm×36 cm, and on the upper surface and the lower surface of each of the absorber having the rectangular shape, water absorbing papers (basic weight: 15.5 g/m²) having the same size as that of the absorber were placed. Furthermore, a polyethylene sheet used for a commercially available disposable diaper was placed on a rear side and a polyethylene non-woven fabric (basic weight: 20.0 g/m²) was placed on the front surface, and thus a disposable diaper was produced.

Evaluations of these disposable diapers in terms of absorption amount under loading, absorption speed under loading, diffusion area under loading, surface dryness, and surface dryness value by SDME are shown in Table 2.

EXAMPLE 25

After forming a layer of 50 parts of fluff pulp, 100 parts of the water absorbing agent (2) obtained in Example 2 was evenly spread, and a layer of 50 parts of fluff pulp further was superimposed thereon to have a sandwich structure, and pressed with a pressure of 5 Kg/cm² for 30 seconds to obtain an absorber (C2). The obtained absorber was cut into a rectangular shape of 14 cm×36 cm, and on the upper surface and the lower surface of each of the rectangular shaped absorber, water absorbing papers (basic weight: 15.5 g/m²) having the same size as that of the absorber were placed. Furthermore, polyethylene sheet used for a commercially available disposable diaper was placed on a rear side and a polyethylene non-woven fabric (basic weight: 20.0 g/m²) was placed on the front surface, and thus a disposable diaper was produced.

Evaluations of these disposable diapers in terms of absorption amount under loading, absorption speed under loading, diffusion area under loading, surface dryness, and surface dryness value by SDME are shown in Table 2.

COMPARATIVE EXAMPLES 4, 5 AND 6

A mixture obtained by mixing 100 parts of fluff pulp and 100 parts of one of the comparative water absorbing agents (1'), (2') or (3') obtained in Comparative Examples 1, 2 and 3 by using an air blender was evenly piled so as to have the basic weight of about 400 g/m² and pressed with a pressure of 5 Kg/cm² for 30 seconds to obtain comparative absorbers (B1'), (B2') or (B3') of Comparative Examples. The obtained absorber was cut into a rectangular shape of 14 cm×36 cm, and on the upper surface and the lower surface of each of the rectangular shape, water absorbing papers (basic weight: 15.5 g/m²) having the same size as that of the absorber were placed on each of the rectangular shaped absorber. Furthermore, a polyethylene sheet used for a commercially available disposable diaper was placed on a rear side and a polyethylene non-woven fabric (basic weight: 20.0 g/m²) was placed on the front surface, and thus a disposable diaper was produced.

Evaluations of these disposable diapers in terms of absorption amount under loading, absorption speed under loading, diffusion area under loading, surface dryness, and surface dryness value by SDME are shown in Table 2.

TABLE 2

| | | Absorber used for disposable diaper | Performance of disposable diaper | | | | |
|---|---|---|---|---|---|---|---|
| | | | Absorption amount under loading (g/sec) | Absorption speed under loading (sec) | Diffusion area under loading (cm²) | Surface dryness | SDME surface dryness value (%) |
| Ex | 13 | B1 | 287 | 355 | 444 | ○ | 75 |
| | 14 | B2 | 266 | 362 | 437 | ○ | 65 |
| | 15 | B3 | 272 | 341 | 450 | ○ | 70 |
| | 16 | B4 | 259 | 353 | 458 | ○ | 62 |
| | 17 | B5 | 263 | 341 | 440 | ○ | 68 |
| | 18 | B6 | 277 | 344 | 445 | ○ | 71 |

TABLE 2-continued

|  | Absorber used for disposable diaper | Performance of disposable diaper | | | | |
|---|---|---|---|---|---|---|
|  |  | Absorption amount under loading (g/sec) | Absorption speed under loading (sec) | Diffusion area under loading (cm$^2$) | Surface dryness | SDME surface dryness value (%) |
| 19 | B7 | 251 | 365 | 440 | ○ | 60 |
| 20 | B8 | 263 | 380 | 445 | ○ | 57 |
| 21 | B9 | 277 | 371 | 440 | ○ | 64 |
| 22 | B10 | 264 | 363 | 435 | ○ | 64 |
| 23 | B11 | 285 | 354 | 443 | ○ | 73 |
| 24 | B12 | 265 | 366 | 437 | ○ | 67 |
| 25 | C2 | 247 | 321 | 427 | ○ | 80 |
| Co. Ex 4 | B1' | 303 | 482 | 356 | Δ | 35 |
| 5 | B2' | 225 | 475 | 329 | Δ | 46 |
| 6 | B3' | 218 | 498 | 319 | Δ | 36 |

Ex.: Examples
Co. Ex.: Comparative Examples

INDUSTRIAL APPLICABILITY

The water absorbing agent of the present invention has the following effects.

<1> The water absorbing agent of the present invention is extremely excellent in the balance in the water-retention performance, the absorption performance under loading and the water permeation speed of hydrogel, as well as the dryness feeling after absorption is exhibited.

<2> When the water absorbing agent is used for sanitary articles such as paper diaper, sanitary napkin, etc., there is not only excellent absorbing performance but also an excellent feature in which absorbed liquid is not easily to return under loading.

Therefore, the water absorbing agent and absorber using the same can be used suitably for absorbent articles etc. capable of exhibiting high absorbing performance in any states.

That is to say, even in the case where the absorbing articles are in a state under loading, for example, where a user sits down or lies down, the absorption amount and the absorption speed are not deteriorated. As a result, it is possible to provide a water absorbing agent suitable for absorbent articles, etc. in which problem such as leakage, etc. are not likely to occur.

The method for producing an absorbing agent of the present invention can easily provide the above-mentioned water absorbing agent of the present invention.

Furthermore, the absorbent articles of the present invention can be preferably used in hygienic materials such as disposable diaper, sanitary napkins, paper towels, pads (incontinence pads, under pads for surgical operations, etc.), pet sheets (pet urine absorption sheet), and the like, and can provide absorbent articles capable of exhibiting high absorbing performance in any states.

The invention claimed is:

1. A water absorbing agent comprising a crosslinked polymer including a water-soluble vinyl monomer (a1) that is free from lithium salts and/or a vinyl monomer (a2) that is formed into the water-soluble vinyl monomer (a1) that is free from lithium salts by hydrolysis, and a crosslinking agent (b) as an essential constituting unit, wherein the following formulae (1) and (2) are satisfied:

$$(Y) \geq -1.14(X) + 69.5 \quad (1)$$

$$(X) = ((x1)^2 + 4 \times (x2)^2)^{1/2} \quad (2)$$

wherein (x1) denotes a water-retention amount (g/g) of the water absorbing agent after being soaked in a physiological saline solution for one hour; (x2) denotes an absorption amount (g/g) of the water absorbing agent after being soaked in a physiological saline solution under loading of 0.9 psi for one hour; and (Y) denotes a liquid permeation speed (ml/min) of a physiological saline solution after the water absorbing agent is soaked in a physiological saline solution under loading of 0.3 psi for one hour.

2. The water absorbing agent according to claim 1, wherein the formula (3) and formula (4) are further satisfied;

$$45 \leq (X) \leq 100 \quad (3)$$

$$2 \leq (Y) \leq 75 \quad (4).$$

3. An absorber comprising the water-absorbing agent according to claim 1 and fibrous materials.

4. An absorbent article comprising the absorber according to claim 3.

5. The water absorbing agent according to claim 1, wherein the water-soluble vinyl monomer (a1) that is free from lithium salts includes at least one selected from the group consisting of acrylic acid and sodium acrylate.

6. The water absorbing agent according to claim 1, wherein the formula (7) and formula (8) are further satisfied;

$$50 \leq (X) \leq 100 \quad (7)$$

$$2 \leq (Y) \leq 25 \quad (8).$$

7. The water absorbing agent according to claim 1, wherein the water-soluble vinyl monomer (a1) consisting essentially of at least one of acrylic acid and sodium acrylate.

8. A water absorbing agent comprising a crosslinked polymer including a water-soluble vinyl monomer (a1) and/or a vinyl monomer (a2) that is formed into the water-soluble vinyl monomer (a1) by hydrolysis and an internal crosslinking agent (1) as an essential constituting unit; wherein at least two of the following conditions <1> to <3> are satisfied:

<1> at least one metallic element (c1) derived from a complex (c) selected from the group consisting of Fe, Co, Ni, Cu, Zn, Ru, Rh, Pd, Ag, Cd, Os, Ir, Pt and Au is contained in the amount of $10^{-9}$ to 1 mass % based on the mass of the crosslinked polymer;

<2> water-insoluble spherical single particles (d) having an average particle size of 1 to 500 nm and having a specific surface area of 20 to 400 m$^2$/g are contained in the amount of 0.1 to 1 mass % based on the mass of the crosslinked polymer; and <3> surface crosslinking is carried out with a surface crosslinking agent (b2), and the standard deviation (S) of the absorbance analyzed by infrared absorption spectrophotometiy of a carbonyl group or an amino group derived from an ester bond or an amide bond is 15 or less with respect to one particle of the crosslinked polymer.

9. The water absorbing agent according to claim 8, wherein the surface crosslinking is carried out with the surface crosslinking agent (b2), and the standard deviation of the absorbance analyzed by infrared absorption spectrophotometry of a carbonyl group or an amino group is 10 or less.

10. The water absorbing agent according to claim 8, wherein the water-insoluble spherical single particle (d) is amorphous silicon oxide.

11. The water absorbing agent according to claim 8, wherein pH (10 mass % aqueous solution) of the water-insoluble spherical single particles (d) is 2 to 11.

12. A method for producing an absorbing agent comprising a crosslinking polymer including a water-soluble vinyl monomer (a1) and/or a vinyl monomer (a2) that is formed into the water-soluble vinyl monomer (a1) by hydrolysis and an internal crosslinking agent (b1) as an essential constituting unit, wherein at least two steps of the following polymerization steps <1> to <3> are included:

<1> a step of polymerization of a crosslinked polymer, including at least one condition selected from the group consisting of (i) to (iii):

(i) the polymerization concentrations of (a1), (a2), other vinyl monomer (a3) capable of co-polymerization and (b1) are $1 \times 10^{-4}$ mass % to 20 mass % based on the total mass of (a1), (a2), (a3), (b1) and a reaction solvent;

(ii) the polymerization temperature is in the range of $(T \pm 5)°$ C. wherein T is 0 to 60; and (iii) the polymerization is carried out in the presence of a complex (c) formed of at least one metal element (c1) selected from the group consisting of Fe, Co, Ni, Cu, Zn, Ru, Rb, Pd, Ag, Cd, Os, I; Pt and Au; and a ligand (c2) including an anion and/or a neutral molecule.

<2> a step of mixing water-insoluble spherical single particles (d) having an average particle size of 1 to 500 nm and a specific surface area of 20 to 400 m$^2$/g with the crosslinked polymer; and <3> a step of surface-crosslinking a crosslinked polymer by a method in which surface crosslinking is carried out with a surface crosslinking agent (b2) to form an ester bond or an amide bond, and the standard deviation (S) of the absorbance analyzed by infrared absorption spectrophotometry of a carbonyl group or an amino group derived from the ester bond or the amide bond is made to be 15 or less with respect to one particle of the crosslinked polymer.

13. The production method according to claim 12, wherein the step <3> of surface-crosslinking is included and the method for making the standard deviation (S) be 15 or less is any of the following methods (i) to (iii);

(i) a method of continuously spraying the surface-crosslinking agent (b2) to a crosslinking polymer particles;

(ii) a method for continuously spraying a solution, an emulsified liquid, or a dispersing liquid including the surface-crosslinking agent (b2);

(iii) a method of allowing a crosslinking polymer particles to flow in a fluidized bed and adding the surface-crosslinking agent (b2) or a solution, an emulsified liquid, or a dispersing liquid thereof.

* * * * *

UNITED STATES PATENT AND TRADEMARK OFFICE
CERTIFICATE OF CORRECTION

PATENT NO. : 7,361,712 B2  Page 1 of 1
APPLICATION NO. : 10/495174
DATED : April 22, 2008
INVENTOR(S) : Munekazu et al.

It is certified that error appears in the above-identified patent and that said Letters Patent is hereby corrected as shown below:

Column 40, Line 60 (Claim 8):    "(1)" should read --(b1)--.
Column 41, Line 9 (Claim 8):     "spectrophotometiy" should read --spectrophotometry--.
Column 41, Line 26 (Claim 12):   "crosslinking" should read --crosslinked--.
Column 42, Line 6 (Claim 12):    "I;" should read --Ir,--.

Signed and Sealed this

Twenty-third Day of December, 2008

JON W. DUDAS
*Director of the United States Patent and Trademark Office*